United States Patent
Sävmarker et al.

(10) Patent No.: US 12,357,573 B2
(45) Date of Patent: *Jul. 15, 2025

(54) PHARMACEUTICAL COMPOSITION FOR DRUG DELIVERY

(71) Applicant: OREXO AB, Uppsala (SE)

(72) Inventors: Jonas Sävmarker, Uppsala (SE); Robert Rönn, Uppsala (SE); Andreas Fischer, Uppsala (SE)

(73) Assignee: OREXO AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/345,770

(22) Filed: Jun. 30, 2023

(65) Prior Publication Data

US 2024/0024244 A1 Jan. 25, 2024

Related U.S. Application Data

(63) Continuation of application No. 17/540,929, filed on Dec. 2, 2021, now Pat. No. 11,737,980, which is a continuation of application No. PCT/GB2021/051191, filed on May 18, 2021.

(30) Foreign Application Priority Data

| May 18, 2020 | (GB) | 2007306 |
| Jun. 29, 2020 | (GB) | 2009905 |
| Dec. 1, 2020 | (GB) | 2018901 |

(51) Int. Cl.
| A61K 9/16 | (2006.01) |
| A61K 9/00 | (2006.01) |
| A61K 31/137 | (2006.01) |

(52) U.S. Cl.
CPC .......... *A61K 9/1652* (2013.01); *A61K 9/1623* (2013.01); *A61K 9/1682* (2013.01); *A61K 31/137* (2013.01); *A61K 9/0078* (2013.01)

(58) Field of Classification Search
None
See application file for complete search history.

(56) References Cited

U.S. PATENT DOCUMENTS

| 5,082,669 | A | 1/1992 | Shirai et al. |
| 5,702,362 | A | 12/1997 | Herold et al. |
| 6,398,074 | B1 | 6/2002 | Bruna et al. |
| 6,938,798 | B2 | 9/2005 | Stradella |
| 7,722,566 | B2 | 5/2010 | Tsutsui |
| 7,947,742 | B2 | 5/2011 | Batycky et al. |
| 8,415,397 | B2 | 4/2013 | Batycky et al. |
| 8,747,813 | B2 | 6/2014 | Batycky et al. |
| 9,724,713 | B2 | 8/2017 | Baillet et al. |
| 9,789,071 | B2 | 10/2017 | Fleming |
| 9,895,444 | B2 | 2/2018 | Maggio |
| 10,039,710 | B2 | 8/2018 | Potta et al. |
| 10,624,864 | B2 | 4/2020 | Sanghvi et al. |
| 10,653,690 | B1 | 5/2020 | Sävmarker et al. |
| 10,688,044 | B2 | 6/2020 | Hartman et al. |
| 10,729,687 | B1 | 8/2020 | Sävmarker et al. |
| 10,792,253 | B2 | 10/2020 | Haruta |
| 10,898,480 | B1 | 1/2021 | Sävmarker et al. |
| 11,077,075 | B2 | 8/2021 | Narayanan et al. |
| 11,400,045 | B2 | 8/2022 | Temtsin-Krayz et al. |
| 2005/0019411 | A1 | 1/2005 | Colombo et al. |
| 2005/0042178 | A1 | 2/2005 | Trunk et al. |
| 2005/0118272 | A1 | 6/2005 | Besse et al. |
| 2007/0202163 | A1 | 8/2007 | Rawas-Qalaji et al. |
| 2008/0269347 | A1 | 10/2008 | Bruss et al. |
| 2009/0264530 | A1 | 10/2009 | Nickell |
| 2011/0045088 | A1 | 2/2011 | Tsutsui et al. |
| 2013/0213398 | A1 | 8/2013 | Lipp et al. |
| 2015/0005356 | A1 | 1/2015 | Fleming |

(Continued)

FOREIGN PATENT DOCUMENTS

| AU | 2006207868 A1 | 9/2006 |
| CN | 1565451 | 1/2005 |

(Continued)

OTHER PUBLICATIONS

Del Valle, "Cyclodextrins and Their Uses: A Review," Process Biochemistry 39:1033-1046 (2004).
Per Gisle Djupesland, "Nasal Drug Delivery Devices: Characteristics and Performance in a Clinical Perspective—A Review," Drug Deliv. and Transl. Res. 3:42-62 (2013).
Fasiolo et al., "Opportunity and Challenges of Nasal Powders: Drug Formulation and Delivery," Eur. J. Pharm. Sci. 113:2-17 (2018).
Florence et al., "The Economic Burden of Prescription Opioid Overdose, Abuse and Dependence in the United States, 2013," Med Care 54(10):901-906 (2016).

(Continued)

*Primary Examiner* — Patricia Duffy
*Assistant Examiner* — Garen Gotfredson
(74) *Attorney, Agent, or Firm* — Troutman Pepper Locke (Rochester)

(57) ABSTRACT

According to the invention, there is provided a pharmaceutically-acceptable composition which is preferably in the form of a spray-dried powder comprising a mixture of:

(a) a pharmacologically-effective dosage amount of at least one pharmaceutically-active compound; and
(b) a pharmaceutically-acceptable carrier material, which carrier material comprises a combination of a disaccharide and a polymeric material.

Compositions are suitable for, for example, transmucosal drug delivery, including sublingual and nasal delivery. In the case of nasal delivery, said compositions may be loaded into single- or multiple-use nasal applicators. Preferred pharmaceutically-acceptable carriers in this regard include lactose or trehalose and dextrins (e.g. cyclodextrins or maltodextrins), which may be spray-dried together in combination. Compositions may further comprise one or more alkyl saccharides. Preferred alkyl saccharides include sucrose esters, such as sucrose monolaurate.

54 Claims, 6 Drawing Sheets

(56) References Cited

U.S. PATENT DOCUMENTS

| | | |
|---|---|---|
| 2015/0018379 A1 | 1/2015 | Strang et al. |
| 2015/0320695 A1 | 11/2015 | Ryoo et al. |
| 2016/0045474 A1 | 2/2016 | Gandhi et al. |
| 2016/0166503 A1 | 6/2016 | Crystal et al. |
| 2016/0235687 A1 | 8/2016 | Prajapati et al. |
| 2016/0374966 A1 | 12/2016 | Rawas-Qalaji et al. |
| 2017/0014341 A1 | 1/2017 | Armer et al. |
| 2017/0071850 A1 | 3/2017 | Vehring et al. |
| 2017/0071851 A1 | 3/2017 | Keegan et al. |
| 2017/0119699 A1 | 5/2017 | Batycky et al. |
| 2017/0319509 A1 | 11/2017 | Canal et al. |
| 2018/0092839 A1 | 4/2018 | Gooberman |
| 2018/0193332 A1 | 7/2018 | Loughlin et al. |
| 2019/0008759 A1 | 1/2019 | Rubin |
| 2019/0070105 A1 | 3/2019 | Amancha et al. |
| 2019/0307156 A1 | 10/2019 | Zasypkin et al. |
| 2020/0316324 A1 | 10/2020 | Hrkach |
| 2022/0087938 A1 | 3/2022 | Sävmarker et al. |
| 2022/0395457 A1 | 12/2022 | Lyman et al. |
| 2023/0310349 A1 | 10/2023 | Sävmarker et al. |
| 2023/0355552 A1 | 11/2023 | Sävmarker et al. |

FOREIGN PATENT DOCUMENTS

| | | |
|---|---|---|
| CN | 1615867 | 5/2005 |
| CN | 1640402 | 7/2005 |
| CN | 1781479 A | 6/2006 |
| CN | 1813739 | 8/2006 |
| CN | 1939358 A | 4/2007 |
| CN | 104547220 A | 4/2015 |
| EP | 0 657 176 A2 | 6/1995 |
| EP | 0 736 299 A1 | 10/1996 |
| EP | 1 093 818 A1 | 4/2001 |
| EP | 1349598 B1 | 11/2004 |
| EP | 2251038 A1 | 11/2010 |
| EP | 3 025 705 A1 | 6/2016 |
| GB | 1 287 475 | 8/1972 |
| JP | 2000178184 A | 6/2000 |
| WO | 91/09592 A1 | 7/1991 |
| WO | 00/62757 A1 | 10/2000 |
| WO | 01/30288 A1 | 5/2001 |
| WO | 01/60338 A1 | 8/2001 |
| WO | 01/87264 A2 | 11/2001 |
| WO | 01/89485 A1 | 11/2001 |
| WO | 02/047607 A2 | 6/2002 |
| WO | 2003/061632 A1 | 7/2003 |
| WO | 2004/054511 A2 | 7/2004 |
| WO | 2004/075877 A1 | 9/2004 |
| WO | 2004/100857 A2 | 11/2004 |
| WO | 2004/112702 A2 | 12/2004 |
| WO | 2005/044186 A2 | 5/2005 |
| WO | 2005/065652 A1 | 7/2005 |
| WO | 2005/079777 A1 | 9/2005 |
| WO | 2006/085101 A2 | 8/2006 |
| WO | 2006/101536 A1 | 9/2006 |
| WO | 2007024123 A1 | 3/2007 |
| WO | 2007/086039 A1 | 8/2007 |
| WO | 2007/096906 A2 | 8/2007 |
| WO | 2007/108010 A2 | 9/2007 |
| WO | 2007/113856 A2 | 10/2007 |
| WO | 2008/033023 A2 | 3/2008 |
| WO | 2008/127746 A1 | 10/2008 |
| WO | 2009/040595 A1 | 4/2009 |
| WO | 2009/120735 A1 | 10/2009 |
| WO | 2010/135495 A2 | 11/2010 |
| WO | 2010/142696 A1 | 12/2010 |
| WO | 2010/144865 A2 | 12/2010 |
| WO | 2011/036521 A2 | 3/2011 |
| WO | 2012/027731 A2 | 3/2012 |
| WO | 2012/042224 A2 | 4/2012 |
| WO | 2012/075455 A2 | 6/2012 |
| WO | 2012/109694 A1 | 8/2012 |
| WO | 2013/168437 A1 | 11/2013 |
| WO | 2014/004400 A2 | 1/2014 |
| WO | 2015/034822 A1 | 3/2015 |
| WO | 2015/091365 A1 | 6/2015 |
| WO | 2015/095389 A1 | 6/2015 |
| WO | 2015/095644 A1 | 6/2015 |
| WO | 2016/016431 A1 | 2/2016 |
| WO | 2016044813 A1 | 3/2016 |
| WO | 2016/055544 A1 | 4/2016 |
| WO | 2016/133863 A1 | 8/2016 |
| WO | 2016/161501 A1 | 10/2016 |
| WO | 2016/179026 A1 | 11/2016 |
| WO | 2017/127641 A1 | 7/2017 |
| WO | 2017/144636 A1 | 8/2017 |
| WO | 2017/158439 A1 | 9/2017 |
| WO | 2017/189947 A1 | 11/2017 |
| WO | 2017/208209 A1 | 12/2017 |
| WO | 2017/218918 A1 | 12/2017 |
| WO | 2018/064377 A1 | 4/2018 |
| WO | 2018/064672 A1 | 4/2018 |
| WO | 2018/089709 A1 | 5/2018 |
| WO | 2018/093666 A1 | 5/2018 |
| WO | 2018/148382 A1 | 8/2018 |
| WO | 2018/195029 A1 | 10/2018 |
| WO | 2019/038756 A1 | 2/2019 |
| WO | 2019/157099 A1 | 8/2019 |
| WO | 2019/241401 A1 | 12/2019 |
| WO | 2020/205663 A1 | 10/2020 |
| WO | 2021/005325 A1 | 1/2021 |
| WO | 2021/234366 A1 | 11/2021 |

OTHER PUBLICATIONS

Górska et al., "The Influence of Trehalose—Maltodextrin and Lactose—Maltodextrin Matrices on Thermal and Sorption Properties of Spray-Dried β-Lactoglobulin-Vitamin D3 Complexes," J. Therm. Anal. Calorim. 112:429-436 (2013).

Hahn & Sucker, "Solid Surfactant Solutions of Active Ingredients in Sugar Esters," Pharm. Res. 6(11):958-960 (1989).

Jüptner et al., "Spray Dried Formulations for Nasal Applications—Challenges and Opportunities in Filling and Drug Delivery," Respiratory Drug Delivery 2:345-348 (2018).

Kürti et al., "The Effect of Sucrose Esters on a Culture Model of the Nasal Barrier," Toxicology in Vitro 26:445-454 (2012).

Li et al., "Non-Ionic Surfactants as Novel Intranasal Absorption Enhancers: In Vitro and In Vivo Characterization," Drug Delivery 23(7):2272-2279 (2016).

Middleton et al., "The Pharmacodynamic and Pharmacokinetic Profile of Intranasal Crushed Buprenorphine and Buprenorphine/Naloxone Tablets in Opioid Abusers," Addiction 106:1460-1473 (2011).

Momin et al., "Investigation Into Alternative Sugars as Potential Carriers for Dry Powder Formulation of Budesonide," BioImpacts 1(2):105-111 (2011).

Naini et al., "Physicochemical Stability of Crystalline Sugars and Their Spray-Dried Forms: Dependence Upon Relative Humidity and Suitability for Use in Powder Inhalers," Drug Development and Industrial Pharmacy 24(10):895-909 (1998).

Pozzoli et al., "Dry Powder Nasal Drug Delivery: Challenges, Opportunities and a Study of the Commercial Teijin Puvlizer Rhinocort Device and Formulation," Drug Development and Industrial Pharmacy 42(10):1660-1668 (2016).

Pozzoli et al., "Development of a Soluplus Budesonide Freeze-Dried Powder for Nasal Drug Delivery," Drug Development and Industrial Pharmacy 43(9):1510-1518 (2017).

Prekupec et al., "Misuse of Novel Synthetic Opioids: A Deadly New Trend," J. Addic. Med. 11(4):256-265 (2017).

Rudd et al., "Increases in Drug and Opioid-Involved Overdose Deaths—United States, 2010-2015," Morbidity and Mortality Weekly Report 65(50-51):1445-1452 (2016).

Russo et al., "Primary Microparticles and Agglomerates of Morphine for Nasal Insufflation," J. Pharm. Sci. 95(12):2553-2561 (2006).

Sacchetti et al., "Caffeine Microparticles for Nasal Administration Obtained by Spray Drying," Int. J. Pharm. 242:335-339 (2002).

Saokham and Loftsson, "γ-Cyclodextrin," Int. J. Pharm. 516:278-292 (2017).

(56) References Cited

OTHER PUBLICATIONS

Szüts and Szabó-Révész, "Sucrose Esters as Natural Surfactants in Drug Delivery Systems—A Mini-Review," Int. J. Pharm. 433:1-9 (2012).

Valdés et al., "Physicochemical Characterization and Cytotoxic Studies of Nonionic Surfactant Vesicles Using Sucrose Esters as Oral Delivery Systems," Colloids and Surfaces B: Biointerfaces 117:1-6 (2014).

Vengerovich et al., "Analysis of the Efficiency of Microencapsulated Sustained-Release Form of Naloxone on the Experimental Model of Fentanyl Poisoning," Bull. Exp. Biol. Med. 163(6):737-741 (2017).

Zhao et al., "Hydroxypropyl-β-Cyclodextrin as Anti-Hygroscopicity Agent Inamorphous Lactose Carriers for Dry Powder Inhalers," Powder Technology 2-11 (2018).

Barnett et al., "Opioid Antagonists," Journal of Pain and Symptom Management 47(2):341-352 (2014).

Thorat S., "Formulation and Product Development of Nasal Spray: An Overview," Scholars Journal of Applied Medical Sciences 4(8D):2976-2985 (2016).

Oliveira et al., "Spray Drying of Food and Herbal Products," Chapter 5 pp. 113-156 (2010).

Mehta P., "Imagine the Superiority of Dry Powder Inhalers from Carrier Engineering," Journal of Drug Delivery 2018:5635010 (2018).

Dowd et al., "Pharmacology and Therapeutics for Dentistry," p. 319 (2010).

Desobry et al., "Influence of Maltodextrin Systems at an Equivalent 25DE on Encapsulated β-Carotene Loss During Storage," Journal of Food Processing and Preservation 23:39-55 (1999).

Gonnissen et al., "Development of Directly Compressible Powders via Co-Spray Drying," Eur. J. Pharm. Biopharm. 67:220-226 (2007).

Kumar et al., "Sugars as Bulking Agents to Prevent Nano-Crystal Aggregation During Spray or Freeze-Drying," Int. J. Pharmaceutics 471:303-311 (2014).

Li et al., "Characterization of Mechanical and Encapsulation Properties of Lactose/Maltodextrin/WPI Matrix," Food Hydrocolloids 63:149-159 (2017).

Lucas et al., "Protein Deposition From Dry Powder Inhalers: Fine Particle Multiplets as Performance Modifiers," Pharmaceutical Research 15(4):562-569 (1998).

Masum et al., "Effect of Lactose-to-Maltodextrin Ratio on Emulsion Stability and Physicochemical Properties of Spray-Dried Infant Milk Formula Powders," J. Food Eng. 254:34-41 (2019).

Pedersen et al., "Solid State Characterisation of a Dry Emulsion: A Potential Drug Delivery System," Int. J. Pharm. 171:257-270 (1998).

Tewa-Tagne et al., "Preparation of Redispersible Dry Nanocapsules by Means of Spray-Drying: Development and Characterisation," Eur. J. Pharm. Sci. 30:124-135 (2007).

Shojaei A.H., "Buccal Mucosa as a Route for Systemic Drug Delivery: A Review," J. Pharm. Pharmaceut. Sci. 1 (1):15-30 (1998).

Gandhi et al., "Oral Cavity as a Site for Bioadhesive Drug Delivery," Adv. Drug Deliv. Rev. 13:43-74 (1994).

Bertram et al., "In Situ Gelling, Bioadhesive Nasal Inserts for Extended Drug Delivery: In Vitro Characterization of a New Nasal Dosage Form," Eur. J. Pharm. Sci. 27:62-71 (2006).

Kou and Zhou, "Amorphous Solid Dispersions," Chapter 16, Shah et al. (Eds.), Springer (2014).

Branchu et al., "Hydroxypropyl-β-cyclodextrin Inhibits Spray-Drying-Induced Inactivation of β-Galactosidase," J. Pharm. Sci. 88(9):905-911 (1999).

Mazzobre et al., "Protective Role of Trehalose on Thermal Stability of Lactase in Relation to its Glass and Crystal Forming Properties and Effect of Delaying Crystallization," Lebensm.-Wiss. u.-Technol. 30:324-329 (1997).

Amaro et al., "Co-Spray Dried Carbohydrate Microparticles: Crystallisation Delay/Inhibition and Improved Aerosolization Characteristics Through the Incorporation of Hydroxypropyl-β-cyclodextrin with Amorphous Raffinose or Trehalose," Pharm Res. 32:180-195 (2015).

Newman et al., "Assessing the Performance of Amorphous Solid Dispersions," Journal of Pharmaceutical Sciences, 101:1355-1377 (2012).

Alpha-D-Lactose monohydrate product page (2015). Retrieved from <https://www.alfa.com/en/catalog/036218/> on May 17, 2022.

Glucidex Maltodextrin 12 product page (2015). Retrieved from <https://www.ulprospector.com/en/eu/Food/Detail/4917/363646/GLUCIDEX-mALTODEXTRIN-12> on May 17, 2022.

Google dated search results for "maltodextrin 12de" May 17, 2022.

Google dated search results for "alpha d lactose monohydrate pharmaceutical" May 17, 2022.

Office Action in U.S. Appl. No. 18/323,115, mailed Nov. 22, 2023.
Office Action in U.S. Appl. No. 18/323,101, mailed Dec. 15, 2023.
Office Action in U.S. Appl. No. 18/323,101, mailed Sep. 11, 2023.
International Search Report and Written Opinion for PCT/GB2022/052996, mailed Jan. 20, 2023.

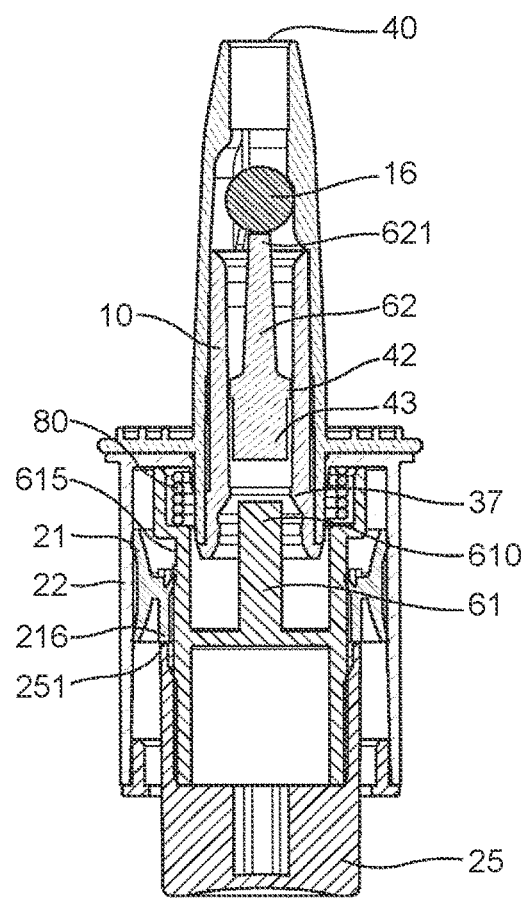
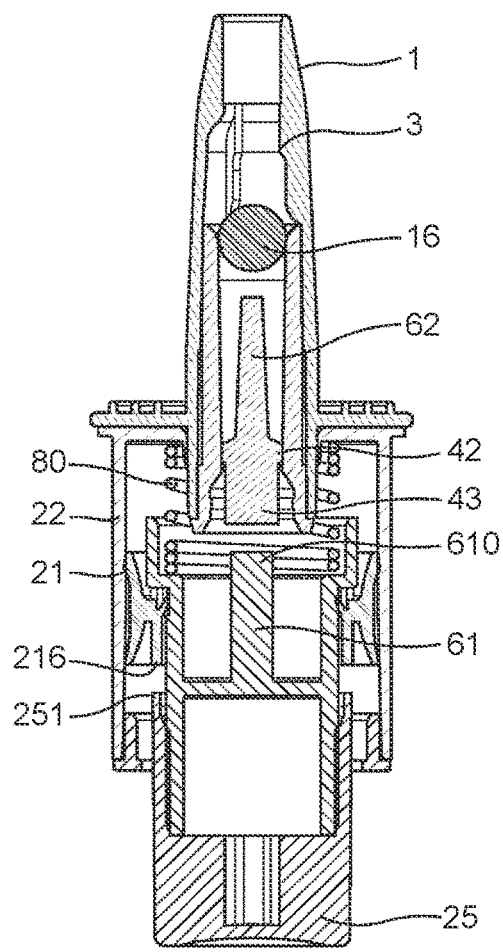
Figure 5                Figure 6
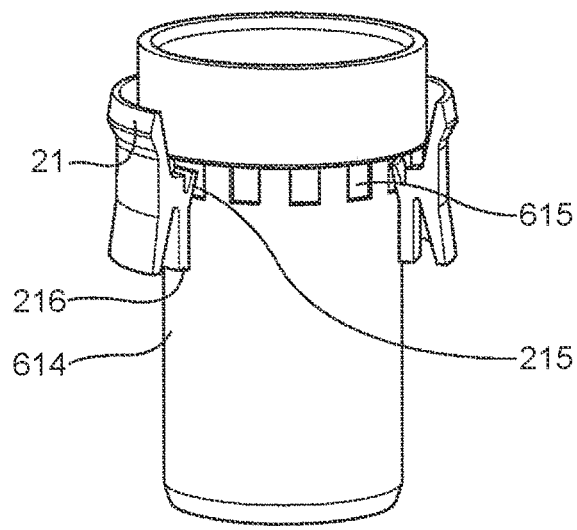
Figure 7

PHARMACEUTICAL COMPOSITION FOR DRUG DELIVERY

This application is a continuation of U.S. patent application Ser. No. 17/540,929, filed Dec. 2, 2021, which is a continuation of PCT Application No. PCT/GB2021/051191, filed May 18, 2021, which is hereby incorporated by reference in its entirety, and which claims the priority benefit of GB 2018901.5, filed Dec. 1, 2020, GB 2009905.7, filed Jun. 29, 2020, and GB 2007306.0, filed May 18, 2020.

This invention relates to new pharmaceutical compositions that are useful in a variety of medical conditions. The invention also relates to methods of manufacturing such compositions and formulating them into dosage forms.

PRIOR ART AND BACKGROUND

The listing or discussion of an apparently prior-published document in this specification should not necessarily be taken as an acknowledgement that the document is part of the state of the art or common general knowledge.

Among the various well-known routes of the drug delivery, peroral delivery to the gastrointestinal tract is the most common. It is generally regarded as being the most favoured by the patients and practitioners.

However, peroral drug administration is known to have specific drawbacks, including the fact that active ingredients are necessarily subject to hepatic first-pass metabolism and also enzymatic degradation within (and outside) the gastrointestinal tract. This may affect the efficacy of certain drugs and, in some cases, may even disqualify it as an administration route altogether.

Peroral administration to the gastrointestinal tract has the additional disadvantage that it requires absorption of active ingredients through the intestines as part of the digestive process, which takes time. In the treatment of certain conditions, such as acute disorders, a more rapid onset of pharmacological effect is often highly desirable.

In such cases, administration principles in which drugs are immediately absorbed into systemic circulation is more likely to lead to a rapid onset of action. Although this can be done via parenteral administration (such as subcutaneous or intravenous injection), such delivery means are inconvenient, and are sometimes very difficult and/or impossible for patients to do, requiring time-consuming intervention by physicians to ensure compliance and avoid effects that are either unwanted or detrimental.

Transmucosal administration of active ingredients is a viable alternative to parenteral administration. It gives rise to the possibility of delivering drug molecules directly into systemic circulation through mucosal membranes (e.g. rectally, sublingually, buccally, pulmonarily and intranasally), and may lead to advantages, such as increased patient compliance, improved drug bioavailability, a more rapid onset of action and reduced side effects.

However, transmucosal administration of drugs presents its own, quite distinct problems. Unlike the gastrointestinal tract, which is a large organ that contains a relatively large amount of biological fluids, spaces such as the oral and nasal cavities are relatively small and contain much lower amounts of bodily fluids, such as saliva and/or mucous. This inevitably provides a considerable limitation on the amount of active ingredient that can be administered in a single dose.

Furthermore, although it is a dynamic system, the gastrointestinal tract is, in the main part, something of a 'closed' system. Conversely, the rapid clearance mechanisms that take place in both the oral and nasal cavities means that the time that is often available for absorption across a mucosal surface, for an already more limited amount of drug, is also limited.

Numerous formulation principles have been put forward to solve this problem, including, for example, bioadhesive formulation principles, such as buccal patches for oromucosal drug delivery (see, for example, Shojaei, *J. Pharm. Pharmaceutical Sci.*, 15, 19 (1998) and Gandhi, *Advanced Drug Delivery Reviews*, 43, 67 (1994)), as well as in situ gelling compositions for intranasal drug delivery (see, for example, Bertan et al, *Eur. J. Pharm. Sci.*, 27, 62 (2006)).

Transmucosal drug delivery systems that are in the solid state may present a significant advantage in allowing for higher drug loadings in the formulation. However, although solid drug delivery compositions are far more common when administering to rectal, buccal, sublingual and pulmonary mucosae, it remains the case that the vast majority of intranasal drug delivery systems are presented in the form of liquid sprays, typically aqueous solutions, wherein drug solubility plays yet another limiting factor in the amount of drug that is available for absorption.

That liquid sprays for intranasal delivery are almost ubiquitous is because formulating solid pharmaceutical formulations in form of a nasal powder is not easy. Unlike powders that are frequently employed for inhalation of active ingredients into the lungs, there are very few commercially-available intranasal powder formulations.

When formulated as dry powders, pulmonary drug delivery compositions typically take the form of 'aggregate' mixtures that include micronized particles of API on larger carrier particles. These aggregates are intended to dissociate/break up upon inhalation or actuation of a device, depositing only the fine particles of active ingredients in the lung.

However, such drug delivery systems are understood not to work effectively in the case of intranasal drug delivery. This is because the presence of such fine particles leads to a significant risk of lung exposure, which is not the intended site of administration. If drug particle sizes were increased to avoid this problem, it would likely lead to difficulties in ensuring appropriate interactions in the heterogeneous 'interactive' mixture, which depends on substantial differences in sizes of the two components to ensure interaction, leading to potential manufacturing issues, such as segregation during filling. Attempting to compensate for this by correspondingly increasing carrier particle size would not necessarily solve the problem, but would necessarily increase the mass of inactive excipients in an already finitely limited total mass of dosage form, potentially resulting in a reduction in the dose of active ingredient.

The difficulties of formulating dry powders for intranasal delivery are dealt with in US Patent Application US 2005/001411 A1. In this document, it is stated that powders for nasal administration need to be fine enough so that they can be efficiently conveyed by a flow of gas and efficiently deposited in the nose, yet also coarse enough to facilitate the introduction of the powder into an appropriate powder device, which is always needed for intranasal administration. US 2005/001411 A1 apparently solves this problem by making loosely formed secondary particles (aggregates) of primary particles comprising active ingredients. The aggregates have dimensions that are a few hundreds of microns, and this is said to enable more efficient loading into an appropriate intranasal administration (an applicator, dispenser or insufflator) device. Upon actuation of such a device, and administration of the composition, the aggregates apparently quickly break up into the primary particles of active ingredients. These primary particles are of a size that is just a few microns, which is stated to facilitate their dissolution and, thereafter, intranasal absorption of active ingredient.

As stated above, transmucosal (e.g. intranasal) delivery of drugs intended for systemic absorption avoids the first pass metabolism that is inevitably a component of peroral administration. Drug metabolism occurs through chemical reactions with enzymes that are capable of altering an active ingredient's chemical structure.

Because most drugs are organic molecules that contain functional groups that are capable of undergoing such chemical reactions, they are often susceptible to some form of chemical decomposition when they come into contact with substances that are capable of interacting with those functional groups outside of the body.

Such chemical transformation is typically classified as chemical 'degradation' in the pharmaceutical field, because it can often lead to a loss of efficacy or, in extreme situations, toxic by-products, either or both of which may lead to a drug being ineffective and/or harmful to patients.

How rapidly such degradation can occur depends upon how inherently chemically-unstable the drug compound is in the first place, the way that it is formulated and the conditions of its storage. Often high temperatures and humidities can lead to accelerated degradation.

Such a loss of chemical integrity is measurable, and is why all pharmaceutical products have shelf-lives printed on their label and/or embossed on their packaging. It is also why certain prescribed medicines contain specific printed information in packaging inserts regarding appropriate storage conditions.

As is summarised by Kou and Zhou in Chapter 16 of the textbook *Amorphous Solid Dispersions*, Shah et al (Eds.), Springer (2014), if a drug is formulated in an amorphous, as opposed to a crystalline, physical state, it is typically presented in a higher energy state, and is thus likely to be more chemically and physically unstable, presenting challenges to pharmaceutical formulators.

Chemical stability is thus often improved by presenting a drug in a crystalline state, often through salt formation. The primary objective of salt formation is usually to increase hydrophilicity of active ingredients in order to address poor aqueous solubility and dissolution rate issues. However, in making a salt, other physicochemical and biological concerns, such as chemical stability, can often be simultaneously addressed. For example, basic drugs (e.g. drugs containing at least one amine group) are often presented in the form of an acid addition salt, which salts are typically more stable chemically than the corresponding 'free' amine bases.

However, whilst potentially providing active ingredient in a form in which it can be more easily stored without chemical degradation, and more efficient in terms of its rate and/or extent of dissolution after administration, crystalline salts generally have slower dissolution rates and are less efficiently absorbed across mucosal membranes, than if corresponding active ingredients are presented in an amorphous, and/or unionized form, respectively.

In summary, active pharmaceutical ingredients formulated as amorphous solid dispersions generally have the advantage of higher bioavailability, but typically present challenges in the form of reduced physical and chemical stability, whereas drugs formulated in a crystalline and/or salt form, whilst generally being more stable tend to be less bioavailable.

The latter problem can be particularly disadvantageous in the case of transmucosal, such as intranasal or sublingual, drug delivery, where, as stated above, residence times of drugs in the relevant cavity, within which absorption into systemic circulation needs to occur, is limited. This, coupled with poor permeability across mucous membranes at physiological pHs may lead to unacceptably low and/or slow transmucosal absorption to provide for an adequate therapeutic effect.

Many elaborate formulation principles have been devised over the years to address the balancing act between solubility and permeability in transmucosal drug delivery systems. Such formulation principles include the addition of pH modifying substances that convert an ionized salt form of active ingredient into a more permeable unionized state.

However, in view of all of the aforementioned potential advantages that it offers, there remains a need for improved solid (e.g. powder-based) transmucosal and especially intranasal drug delivery systems.

In particular, there remains a significant unmet clinical need in the field of transmucosal delivery, for a powdered drug delivery composition that:
(i) is both physically and chemically stable; and
(ii) provides active ingredient:
  at a sufficient dose; and
  in a form in which it is permeable enough
  to provide a required therapeutic effect (such as speed of onset) at the (relatively speaking) low doses that are possible, and short residence times that are available, in the transmucosal context, such as within the nasal cavity.

In addition to the above, in the more specific field of intranasal drug delivery, there remains a significant unmet clinical need for such a drug delivery composition that comprises particles of an appropriate size to enable both the efficient:
  filling of a drug delivery device; and
  deposition within the relevant (e.g. nasal) cavity.

Intranasal dry powder formulations are known from inter alia international patent applications WO 2010/142696 and WO 2019/038756, U.S. Pat. No. 10,653,690 B1 and US patent application US 2018/0092839A.

Russo et al (*J. Pharm. Sci.*, 95, 2253 (2006)) discloses spray-drying the opioid analgesic compound, morphine, with numerous excipients. Spray-dried formulations are also disclosed in Vengerovich et al., *Bulletin of Experimental Biology and Medicine*, 163, 737 (2017), where it was attempted to microencapsulate an active ingredient (naloxone) in various substances, including 2-hydroxypropyl-β-cyclodextrin, with a view to developing sustained-release preparations based on polymeric carriers for emergency care.

We have now found that it is possible to formulate certain active ingredients in the form of amorphous dry powder compositions by way of a process that, for example, spray-dries those active ingredients along with a specific combination of carrier materials, as disclosed hereinafter. Such compositions may provide for surprising and substantial improvements in stability of those active ingredients before administration. Such compositions may in addition provide for improved bioavailability and/or speed of absorption of those active ingredients following administration.

BRIEF DESCRIPTION OF THE DRAWINGS

FIGS. 1 to 7 represent drawings of actuator devices that may be used to dispense compositions of the invention.

DISCLOSURE OF THE INVENTION

Figures 1, 2:
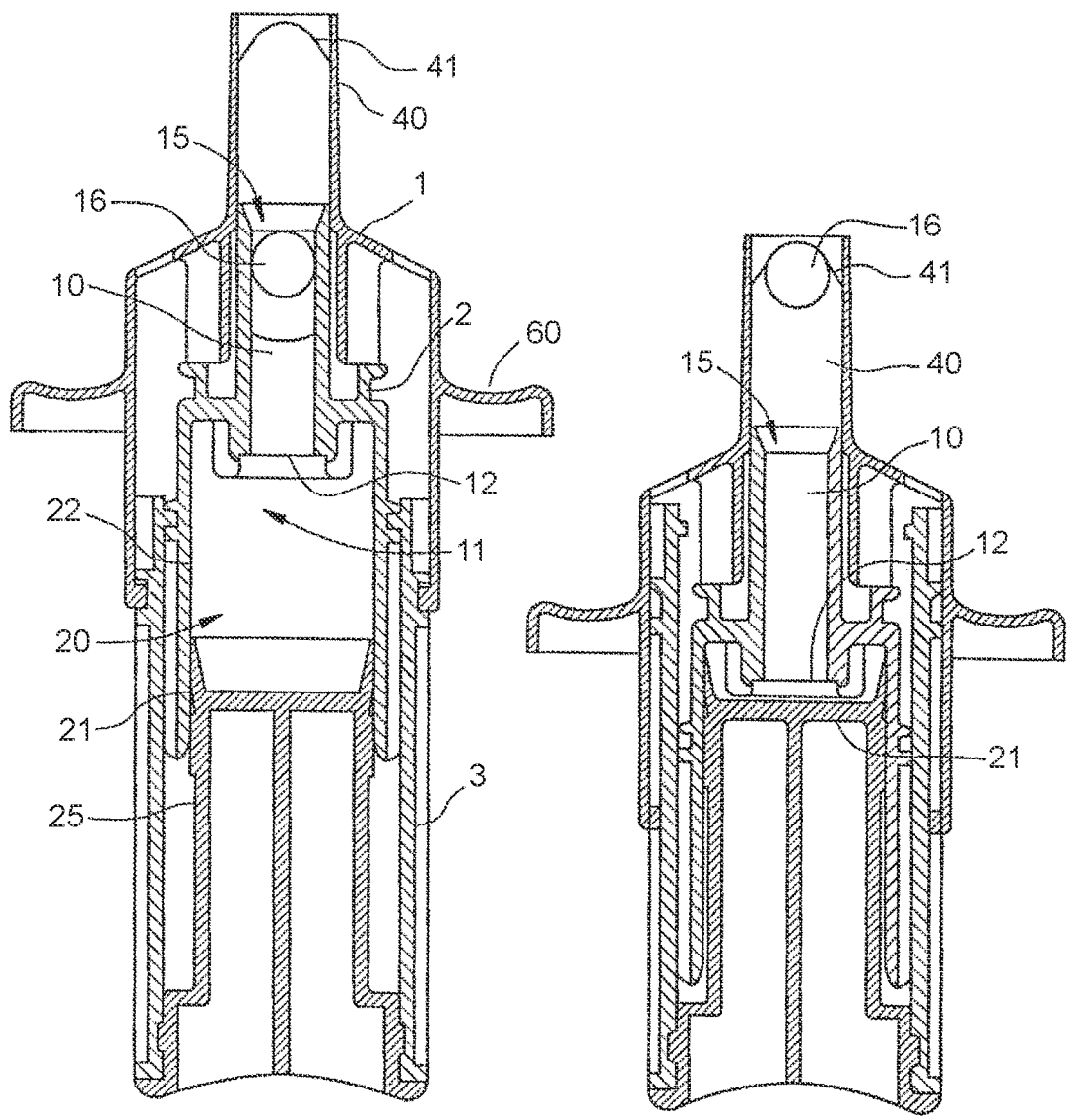
Figure 3:
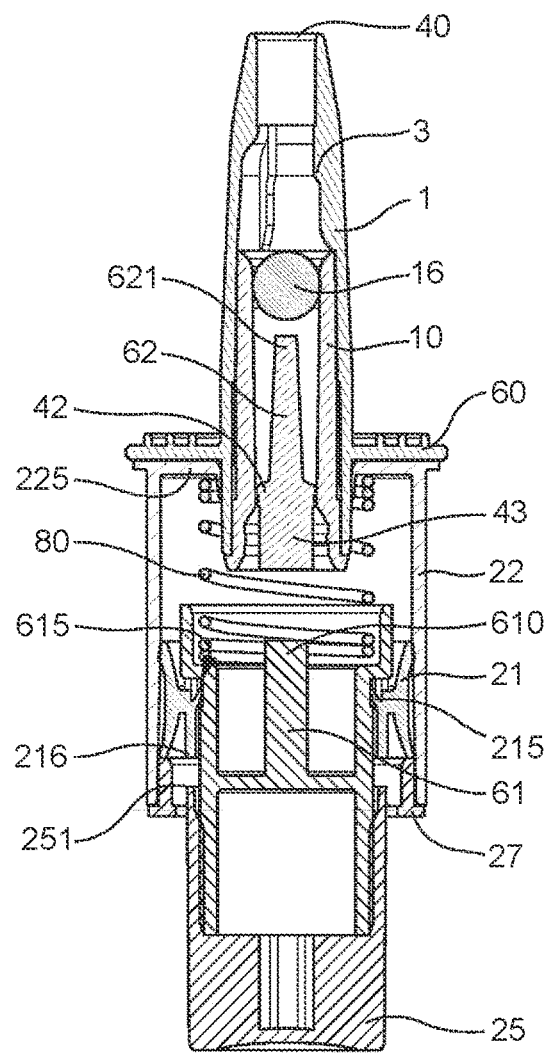

According to a first aspect of the invention, there is provided a pharmaceutically-acceptable composition in the form of an amorphous, mono-particulate powder comprising a mixture of:
(a) a pharmacologically-effective dosage amount of at least one pharmaceutically-active compound; and
(b) a pharmaceutically-acceptable carrier material, which carrier material comprises a combination of a disaccharide and a polymeric material,
which pharmaceutically-acceptable compositions are referred to hereinafter together as 'the compositions of the invention'.

Compositions of the invention are in the form of an amorphous, mono-particulate powder. By 'mono-particulate', we mean that the plurality of particles that form the powdered compositions of the invention comprise a homogeneous or a heterogeneous mixture, in which pharmaceutically-active ingredients are encapsulated in an amorphous state within the carrier materials as defined above, optionally in the presence other ingredients. The particles of the powdered compositions of the invention are thus presented as an amorphous composite of active ingredient, the aforementioned carrier materials and, optionally, other ingredients.

By being amorphous in their nature, compositions of the invention may be wholly amorphous and/or predominantly amorphous (for example more than about 50% by weight, such as more than about 75% by weight, including more than about 80% by weight, such as more than about 90% by weight, or 95% by weight, including more than about 99% by weight amorphous).

As described hereinafter, despite being in an amorphous physical state, compositions of the invention exhibit remarkable and unexpected physical and chemical stability, and may thus be provided in the form of pharmaceutical products that show excellent shelf-life when stored under normal storage conditions.

Compositions of the invention are produced in the form of solid powders by an appropriate technique. In general, appropriate techniques fall into 'solvent-based' methods, which include spray-drying, fluidized bed techniques, co-precipitation, supercritical fluid techniques, spray granulation, cryogenic techniques (including freeze-drying), electrospinning and rotating jet techniques, or 'fusion-based' methods, which include melt granulation, melt extrusion, high-shear mixing (e.g. KinetiSol®), milling and molten material on carrier techniques (e.g. Meltdose®). Preferred methods include freeze-drying and, more preferably, compositions of the invention are made by a process of spray drying.

Such powders may be suitable for delivery via any pharmaceutically-acceptable administration route directly to patients, or may be presented as an intermediate composition that may subsequently be formulated into a pharmaceutically-acceptable dosage form which is to be administered to one or more patients.

In this respect, there is provided a pharmaceutical formulation and/or a pharmaceutically-acceptable dosage form which formulation and/or dosage form is to be administered to a patient, and comprises one or more compositions of the invention.

Suitable pharmaceutical dosage forms may thus comprise liquid formulations, such as solutions, which may be prepared by dissolving a composition of the invention in a pharmaceutically-acceptable solvent (such as water), for delivery to such patients for example by injection or by infusion.

Alternative pharmaceutical dosage forms may comprise liquid or semi-solid formulations, such as liquid suspensions and/or gel compositions which may comprise (e.g. particles of) a composition of the invention that is/are suspended or dissolved in an appropriate liquid or semi-solid carrier which may be loaded into an appropriate dosage form or delivered by, for example, injection or infusion, or may be formed after injection (e.g. subcutaneously or intramuscularly) to form an implant or a depot formulation.

Compositions of the invention may in the alternative be presented as part of an essentially solid pharmaceutical dosage form. The term 'solid' will be well understood by those skilled in the art to include any form of matter that retains its shape and density when not confined, and/or in which molecules are generally compressed as tightly as the repulsive forces among them will allow. An essentially solid formulation is thus one that is at least about 80%, such as at least about 90%, including at least about 95% (or at least about 99%) in such a form.

In this respect, compositions of the invention may be provided in a multi-particulate form (e.g. as powders, granules, pellets and/or beads), comprising a plurality of particles that may individually and/or may collectively consist essentially of, and/or comprise, one or more compositions of the invention.

Compositions of the invention may thus be presented following their preparation (e.g. by spray-drying) in the form of simple powder mixtures, powder microspheres, coated powder microspheres, a lyophilised liposomal dispersion, or a combination thereof.

If a pharmaceutically-acceptable dosage form of the invention 'consists essentially of' the particles of one or more compositions of the invention, this will be understood to mean that that dosage form comprises only one or more compositions of the invention, along with other features that do not materially affect the basic and novel characteristic(s) of the dosage form. Alternatively, in situations where the dosage forms of the invention 'consist essentially of' one or more compositions of the invention, this may be understood to mean that that dosage form comprises at least about 90%, such as at least about 95%, including at least about 97% (e.g. about 99%) by weight of those one or more compositions of the invention in total.

Pharmaceutical dosage forms may in the alternative comprise one or more compositions of the invention, which may be provided in the form of a single unit dosage form, such as a pessary, a suppository or another form of insert, a pill, a capsule, a cake, a patch (e.g. a buccal patch), a film (e.g. an intraoral film) or a tablet (e.g. a sublingual tablet).

Capsules may be prepared by loading a composition of the invention as a spray-dried powder directly into a pharmaceutically-acceptable capsule made from an appropriate material designed for either sublingual or, preferably, peroral delivery, or by mixing a composition along with excipients prior to loading into such a capsule, which may involve a granulation step as described hereinafter, prior to loading into a capsule for such delivery.

Compositions of the invention may in this respect be granulated into a pellet or a pill, but they may also be formulated (that is, provided for administration) in the form of a dry, free-flowing powder. By 'dry' we include essentially free of water and other liquid solvents, which includes that there is less than about 10%, such as less than about 5%, more preferably about 3%, such as less than about 2%, e.g. less than about 1% of the formulation is a liquid, such as water.

Appropriate techniques for making dosage forms comprising dry powders or granulates include simple dry mixing, granulation (including dry granulation, wet granulation, melt granulation, thermoplastic pelletising, spray granulation), extrusion/spheronisation or freeze-drying.

Dry granulation techniques are also well known to those skilled in the art and include any technique in which primary powder particles are aggregated under high pressure, including slugging and roller compaction, for example as described hereinafter.

Wet granulation techniques are well known to those skilled in the art and include any technique involving the massing of a mix of dry primary powder particles using a granulating fluid, which fluid comprises a volatile, inert solvent, such as water, ethanol or isopropanol, either alone or in combination, and optionally in the presence of a binder or binding agent. The technique may involve forcing a wet mass through a sieve to produce wet granules which are then dried, preferably to a loss on drying of less than about 3% by weight.

Melt granulation will be known by those skilled in the art to include any technique in which granules are obtained through the addition of a molten binder, or a solid binder which melts during the process (which binder materials may comprise the pharmaceutically acceptable carrier materials of the composition of the invention). After granulation, the binder solidifies at room temperature. Thermoplastic pelletising will be known to be similar to melt granulation, but in which plastic properties of the binder are employed. In both processes, the agglomerates (granules) obtained comprise a matrix structure.

Extrusion/spheronisation will be well known to those skilled in the art to include any process involving the dry mixing of ingredients, wet massing along with a binder, extruding, spheronising the extrudate into spheroids of uniform size, and drying.

Spray granulation will be known by those skilled in the art to include any technique involving the drying of liquids (solutions, suspensions, melts) while simultaneously building up granulates in a fluid bed. The term thus includes processes in which foreign seeds (germs) are provided upon which granules are built up, as well as those in which inherent seeds (germs) form in the fluid bed due to abrasion and/or fracture, in addition to any spray coating granulation technique generally. The sprayed liquid coats the germs and assists further agglomeration of particles. It is then dried to form granules in the form of a matrix.

The term 'freeze drying' includes lyophilisation or cryodesiccation, and any low temperature desolvatization (e.g. dehydration) process, in which product is frozen, pressure is lowered, and the frozen solvent (e.g. water) is removed by sublimation.

Compositions of the invention may in the alternative be provided in the form of a tablet for peroral, buccal and/or sublingual use. Such tablets may be formed for example by direct compression/compaction of a composition of the invention, optionally following mixing it together with one or more appropriate excipients, such as a diluent, a disintegrant, a glidant and/or a lubricant, and may be achieved using techniques such as those described in, for example, *Pharmaceutical Dosage Forms: Tablets. Volume 1*, $3^{rd}$ Edition, Augsburger et al (eds.), CRC Press (2008) and the documents cited therein. Suitable compacting equipment includes standard tabletting machines, such as the Kilian SP300 or the Korsch EKO, XP1, XL 100, and XL 200.

Suitable disintegrants (as defined in, for example, Rowe et al, *Handbook of Pharmaceutical Excipients*, $6^{th}$ ed. (2009)) that may be employed in tablets include cellulose derivatives such as hydroxypropyl cellulose (HPC), low substituted HPC, methyl cellulose, ethyl hydroxyethyl cellulose, carboxymethyl cellulose calcium, carboxymethyl cellulose sodium, microcrystalline cellulose, modified cellulose gum; starch derivatives such as moderately cross-linked starch, modified starch, hydroxylpropyl starch and pregelatinized starch; and other disintegrants such as calcium alginate, sodium alginate, alginic acid, chitosan, colloidal silicon dioxide, docusate sodium, guar gum, magnesium aluminium silicate, polacrilin potassium and polyvinylpyrrolidone. Combinations of two or more disintegrants may be used.

Preferred disintegrants include so-called superdisintegrants' (as defined in, for example, Mohanachandran et al, *International Journal of Pharmaceutical Sciences Review and Research*, 6, 105 (2011)), such as cross-linked polyvinylpyrrolidone, sodium starch glycolate and croscarmellose sodium. Combinations of two or more superdisintegrants may be used.

When disintegrants and/or superdisintegrants are employed tablets in an (e.g. total) amount of between 0.5 and 15% by weight based upon the total weight of a composition. A preferred range is from 1 to 8%, such as from about 2 to about 7% (e.g. about 5%, such as about 4%) by weight.

If present, binder is preferably employed in an amount of between 0.5 and 20% by weight based upon the total weight of the tablet formulation. A preferred range is from 1 to 15%, such as from about 2.0 to about 12% (e.g. about 10%) by weight. Suitable binders include cellulose gum and microcrystalline cellulose.

Whether in the form of a powder or otherwise, dosage forms comprising compositions of the invention may otherwise be prepared by standard techniques, and using standard equipment, known to the skilled person. In this respect, the compositions of the invention may be combined with conventional pharmaceutical additives and/or excipients used in the art for relevant preparations, and incorporated into various kinds of pharmaceutical preparations using standard techniques in order to make dosage forms of the invention (see, for example, Lachman et al, *The Theory and Practice of Industrial Pharmacy*, Lea & Febiger, $3^{rd}$ edition (1986); '*Remington: The Science and Practice of Pharmacy*', Troy (ed.), University of the Sciences in Philadelphia, $21^{st}$ edition (2006); and/or '*Aulton's Pharmaceutics: The Design and Manufacture of Medicines*', Aulton and Taylor (eds.), Elsevier, $4^{th}$ edition, 2013).

It is preferred that compositions of the invention are suitable for, and/or are formulated for, transmucosal delivery of the active ingredient into systemic circulation.

The term 'transmucosal' will be understood by those skilled in the art to mean that, however it is administered to a patient, a composition is presented at a relevant mucosal surface in such a form that the active ingredient(s) may be absorbed across that mucosal surface following its dissolution. Relevant mucosal surfaces thus include the oral, nasal, ocular, vaginal, cervical, pulmonary and/or anorectal mucosae, more particularly the oral mucosa (including buccal and sublingual mucosae) and the nasal mucosa.

Thus, dosage forms comprising a composition of the invention may be directly administered to a mucosal surface (including rectally, vaginally, buccally, sublingually or intranasally) of a patient for transmucosal delivery of active ingredients.

If administered to the sublingual mucosa, compositions of the invention may be in the form of e.g. sublingual tablets as described above, which may comprise disintegrantsor disintegrating agents (which may be defined as any material that is capable of accelerating to a measurable degree the disintegration/dispersion of such composition of the invention), which may be achieved, for example, by the material being capable of swelling and/or expanding when placed in contact with aqueous media, as described hereinafter.

Alternatively compositions of the invention may be administered sublingually in the form of a powder as described herein, which may be emptied into the mouth and under the tongue from an appropriate receptacle, such as a capsule or a sachet.

If compositions of the invention are suitable for, and/or are formulated for sublingual or, more notably, intranasal administration, then they are preferably administered in the form of a powder composition in which the dosage amount of the active ingredient(s) is no more than about 100 mg. Such sublingual and/or nasal powder compositions may comprise a composition of the invention admixed with other excipients, or may consist essentially of a composition of the invention as hereinbefore defined.

Compositions of the invention that are suitable for, and/or are formulated for, intranasal administration are preferably provided by way of a dosing means that is suitable for nasal delivery. Such a dosing means may contain one spray-dried powder composition of the invention, or it may contain two or more such compositions. In the latter instance, the dosing means contains two or more dosing amounts of said composition of the invention, which dosing amounts will each contain a pharmacologically-effective dose of the pharmacologically-active compound(s) (also referred to herein interchangeably as 'drug(s)', 'pharmaceutically-active ingredient(s) and/or 'active ingredient(s)').

Two or more compositions of the invention may be administered intranasally, either by repeated actuation of a device that either comprises, or is in communication with, that dosing means. Compositions of the invention may therefore be presented within an appropriate device (e.g. a nasal applicator or dispenser (insufflator), for example as described hereinafter), and/or may be presented within a container or a reservoir that is part of, is adjunct to, and/or is suitable for being placed adjunct to, such an applicator. Such a container or reservoir may contain the one or more compositions of the invention, each containing a pharmacologically-effective dosage amount of said active ingredients.

In this way, appropriate dosing means and/or nasal applicators may be actuated only once to deliver a single composition of the invention comprising an appropriate dose of an active ingredient following that actuation (i.e. a single-use dosing unit), may be actuated more than once to deliver two or more compositions of the invention, each comprising an appropriate dose of active ingredient, upon each such actuation (i.e. a multiple-use dosing unit), and/or may be re-filled with a replacement source of composition(s) of the invention (e.g. a container or reservoir), comprising one or more such compositions, to provide for single and/or multiple doses and/or dosing regimens.

Compositions of the invention may thus be administered in the form of a plurality of particles, which particles may individually and/or collectively consist of, and/or comprise, compositions of the invention.

Compositions of the invention are thus prepared (initially) in the form of solid, dry, free-flowing, multi-particulate powders. By 'dry' we include essentially free of water and other liquid solvents, which includes that there is less than about 10%, such as less than about 5%, more preferably about 3%, such as less than about 2%, e.g. less than about 1% of the formulation is a liquid, such as water.

As stated above, compositions of the invention are provided in the form of amorphous, mono-particulate powders. They are not composed of physical associations of two or more discrete, separate sets of particles of different ingredients in the form of a mixture, such as an ordered, or interactive, mixture of smaller particles of active ingredients associated with larger, but separate and chemically distinct, particles of carrier substances. That said, compositions of the invention may be provided as small particles which may subsequently be adhered to separate, larger carrier particles in an interactive mixture, and such a presentation may be useful if the dosage form that is intended for inhalation, for example to the lung, (see e.g. *J. Drug Delivery*, Art. ID 5635010, 1-19 (2018)).

As mentioned hereinbefore, the process of making compositions of the invention enables the formation of pharmaceutical products that show excellent shelf-life, in terms of both physical and chemical stability, when stored under normal storage conditions, as defined herein.

Compositions of the invention are preferably prepared by a process of spray-drying. The process of 'spray-drying' will be understood by the skilled person to include any method of producing a dry powder from a liquid, including a solution or a suspension (including a slurry) that involves rapid drying using hot gas to convert a stream of liquid into vaporized solvent and particles of solid, which solid particles comprise the solute that was previously dissolved in a solution, and/or particles that were previously suspended in the evaporated liquid.

Appropriate spray-drying equipment includes some form of atomization means, such as a spray nozzle, which disperses the liquid into a spray with a relatively uniform droplet size. Such means may include any means that is capable of producing a dry, free-flowing powder, and may include high pressure swirl nozzles, rotary disks and/or atomizer wheels, high pressure single fluid nozzles, two-fluid nozzles and/or ultrasonic nozzles.

The spray-dryer may be a single effect or a multiple effect spray-dryer, and may comprise an integrated and/or an external vibrating fluidized bed, a particle separator, and/or a collection means which may be a drum or a cyclone.

According to a further aspect of the invention, there is provided a process for the manufacturing of a composition of the invention, wherein said process comprises the steps of:

i) mixing together the one or more active ingredients and pharmaceutically-acceptable carrier materials, in an appropriate volatile solvent, ii) spray-drying the mixture from step i).

Preferred volatile solvents include water, or organic solvents, such as lower alkyl alcohols (e.g. ethanol), hydrocarbons (e.g. $C_{5-10}$ alkanes), haloalkanes, dimethylformamide, dimethylsulfoxide, ethyl acetate, acetone, etc., or mixtures thereof.

We prefer that mixing together the one or more active ingredients, pharmaceutically-acceptable carrier materials, and other optional ingredients as described herein (for example alkyl saccharides as described hereinafter), with the solvent results in a solution that can be spray-dried.

Appropriate pharmaceutically-acceptable carrier materials that may be employed in compositions of the invention include relevant materials that, in the appropriate combination, are suitable (and/or approved) for pharmaceutical use and/or for transmucosal (e.g. sublingual or, notably, intranasal) delivery, and are capable of maintaining their physical and/or chemical integrity, and/or do not affect the physical and/or chemical integrity of any active ingredients and/or any other ingredients that are or may be present in the composition (such as alkyl saccharide), in the solid state, under normal storage conditions.

It is well known that significant difficulties may be experienced in attempting to obtain both chemically- and physically-stable solid compositions, such as powders. If the physical form of a composition changes under normal storage conditions (e.g. from a free flowing powder to an agglomerated mass that is difficult to discharge), it will likely lead to non-reproducibility of dose of active ingredient. This is particularly so when dispensing a composition from, or via, a nasal applicator as described herein, where such agglomeration may result in the complete inability to dispense the active ingredient.

Similarly, for multiple dose units containing two or more doses of a composition, such stability is critical to ensure reproducibility of the dose of active ingredient over time. Either of these problems may have a detrimental effect on a subject's health, and/or put a subject's well-being at significant risk.

For certain compositions of the invention, exposure to atmospheric water may result in powder compositions that are less solid-state stable. For example, exposure to certain (e.g. higher) relative humidities may affect the physical form of the composition, for example by deliquescence, and/or by lowering glass transition temperatures of compositions, and/or individual components of the compositions, such as carrier materials, or in another way.

Accordingly, compositions of the invention, and pharmaceutical formulations and dosing means (such as nasal applicators) including them, are preferably packaged within containers that substantially prevent the ingress of atmospheric water under the storage conditions defined herein. Such containers may include packaging materials, such as blister packs for tablets and capsules and heat-sealed aluminium pouches and/or thermoformed plastics.

The phrase 'maintaining physical and chemical integrity' essentially means chemical stability and solid state stability.

By 'chemical stability', we include that any composition of the invention may be stored in isolated solid form, when formulated into a pharmaceutical formulation or dosage form, and/or when loaded into a pharmaceutical dosing means, such as a nasal applicator or a reservoir therefor (with or without appropriate pharmaceutical packaging), under normal storage conditions, with an insignificant degree of chemical degradation or decomposition of either the composition per se or the active ingredient included therein.

By 'solid state stability', we include that any composition of the invention may be stored in an isolated solid form, when formulated into a pharmaceutical formulation or dosage form, and/or when loaded into a pharmaceutical dosing means, such as a nasal applicator or a reservoir therefor (with or without appropriate pharmaceutical packaging), under normal storage conditions, with an insignificant degree of solid state transformation (e.g. crystallisation, recrystallisation, loss of crystallinity, solid state phase transition (e.g. between a glassy or a rubbery state, or to an agglomerated form)), hydration, dehydration, solvatisation or desolvatisation of either the composition per se or the active ingredient included therein.

Examples of 'normal storage conditions' for compositions of the invention, whether in the form of a pharmaceutical formulation or dosage form, and/or when loaded into a pharmaceutical dosing means loaded into applicators, devices, drug reservoirs (such as canisters or containers) or otherwise, include temperatures of between about −50° C. and about +80° C. (preferably between about −25° C. and about +75° C., such as about 50° C.), and/or pressures of between about 0.1 and about 2 bars (preferably atmospheric pressure), and/or exposure to about 460 lux of UV/visible light, and/or relative humidities of between about 5 and about 95% (preferably about 10 to about 40%), for prolonged periods (i.e. greater than or equal to about twelve, such as about six months).

Under such conditions, compositions of the invention (and/or active ingredients contained therein) may be found to be less than about 15%, more preferably less than about 10%, and especially less than about 5%, chemically degraded/decomposed, and/or solid-state transformed, as appropriate. The skilled person will appreciate that the above-mentioned upper and lower limits for temperature and pressure represent extremes of normal storage conditions, and that certain combinations of these extremes will not be experienced during normal storage (e.g. a temperature of 50° C. and a pressure of 0.1 bar).

Such chemical and, particularly, physical stability is of importance in a solid state composition, such as a powder, to ensure that the appropriate dose is delivered to the patient. This is particularly so when the composition is to be delivered intranasally.

Particularly preferred pharmaceutically-acceptable carrier materials that may be employed to produce compositions of the invention, and which possess the desirable characteristics mentioned herein, include, for the disaccharide component, maltitol, trehalose, sucralose, sucrose, isomalt, maltose and, particularly, lactose (including β-D-lactose and α-D-lactose, especially α-D-lactose monohydrate)

For the polymeric material component, preferred pharmaceutically-acceptable carrier materials that may be employed to produce compositions of the invention, and which possess the desirable characteristics mentioned herein, include cellulose and its derivatives, such as sodium carboxymethyl cellulose, ethyl cellulose, cellulose acetate, hydroxypropylmethyl cellulose (hypromellose, HPMC), hydroxyethyl cellulose (HEC), hydroxypropyl cellulose (HPC), methyl cellulose (MC), ethyl hydroxyethyl cellulose, carboxymethyl cellulose (CMC), modified cellulose gum, microcrystalline cellulose and sodium carboxymethyl cellulose; starches, such as rice starch, tapioca starch, wheat starch and, more particularly, corn starch and potato starch; starch derivatives, such as pregelatinized starch, carboxymethyl starch, as well as moderately cross-linked starch, modified starch and sodium starch glycolate; polysaccharides, including dextrins, such as dextrin, cyclodextrins and linear or branched dextrins, such as maltodextrins; powdered tragacanth; waxy excipients, such as cocoa butter and suppository waxes; polyols, such as solid polyethylene glycols; acrylic polymers, such as carbomer and its derivatives; polyvinylpyrrolidone (povidone, PVP); crosslinked polyvinylpyrrolidone; polyethylene oxide (PEO); chitosan (poly-(D-glucosamine)); natural polymers, such as gelatin, sodium alginate, pectin; scleroglucan; xanthan gum; guar gum; poly co-(methylvinyl ether/maleic anhydride); and croscarmellose (e.g. croscarmellose sodium). Hypromellose acetate succinate (HPMCAS), copovidone and polyvinyl alcohol (PVA, or PVOH) may also be mentioned.

More preferred polymeric materials include sodium carboxymethyl cellulose, sodium starch glycolate, polyvinylpyrrolidone and, particularly, hydroxypropylmethyl cellulose (such as hypromellose 2906, preferably hypromellose 2910 (i.e. 'E'-types), and more preferably USP/NF hypromellose 2208 (i.e. 'K'-types)), and the like, or, particularly, polysaccharides, such as dextrins, including cyclodextrins (e.g. α-, β- and γ-cyclodextrins and derivatives thereof, such as, 2-hydroxypropyl-γ-cyclodextrin, sulfobutylether β-cyclodextrin sodium salt, randomly methylated β-cyclodextrin, branched β-cyclodextrin and the like and, particularly, 2-hydroxypropyl-8-cyclodextrin); and linear or branched dextrins, such as maltodextrins, which are classified by DE (dextrose equivalent), which can be between 3 and 20 (the higher the DE value, the shorter the average length of the glucose chains), especially maltodextrin with a DE of between 6 and such as 8 and 12.

In any event, suitable polymers for use in compositions of the invention should have a molecular weight that is high enough such that, when it is employed in any given amount in combination with a disaccharide, it is capable of forming a suitable carrier material for the active ingredient.

For any given polymer, polymer chain length (and therefore molecular weight) is directly proportional to its viscosity. Put another way, the viscosity of a solution of that polymer is proportional to the molecular weight or chain length of the specific polymer.

In this respect, it may be preferred that the polymer has a relative viscosity value at 20° C. of no more than about 1000 (more preferably no more than about 120, such as no more than about 60, and particularly no more than about 10) mPa*s, as measured, for any given and essentially:
 (a) water-soluble polymer, as a 2 wt % solution of the polymer in water by the standard USP methods for viscosity, i.e. <911> Method I, and/or <912> Method I; and
 (b) water-insoluble polymer, as a 5 wt % solution of the polymer in a suitable organic solvent, such as acetone, methanol, ethanol, isopropyl alcohol, ethyl acetate, acetonitrile, dichloromethane, toluene and mixtures thereof, which solvent system may be dry or partly aqueous, by the USP method <911> Method I.

The skilled person will understand which test is more suitable for the polymer tested.

Mixtures from any of the foregoing lists of disaccharides and/or polymeric materials may be employed.

Amounts of carrier materials that may be employed in compositions of the invention are typically in the range of about 5% to about 99.9%, including up to about 99% (e.g. up to about 95% or about 90%), such as about 10% (e.g. about 25%, including about 35%) to about 85%, including about 50% to about 75%, by weight, based upon the total weight of the composition (whether one dose of said composition is included in the dosing means or otherwise).

It is preferred that the combination of carrier materials is capable of giving rise to a composition of the invention that possesses a glass transition temperature (Tg) that:
 (a) enables its production as a hard and/or brittle, 'glassy', amorphous, powdered physical form, that can be easily formulated into a pharmaceutical formulation or dosage form, and/or loaded into a suitable dosing means, such as a nasal applicator, or a drug reservoir and/or container within, or adjunct to, such an applicator, as described herein; and
 (b) is high enough that, after such a pharmaceutical formulation, dosage form or dosing means, such as an applicator or reservoir, is packaged as described herein, and thereafter subjected to a high external temperature (e.g. up to between about 50° C. and about 80° C.), it remains in that glassy state, rather than being transformed into a more viscous or rubbery state, and/or a crystalline state.

Such extreme external temperatures are often experienced inside vehicles in warm and/or sunny climates, which vehicles will frequently be parked for extended periods of time in full sun, where the resultant heat gain can be enormous. If the Tg of a composition of the invention is low, the composition may transform after exposure to such high temperatures to such a viscous/rubbery state, this will give rise to inefficient dosing of the composition of the invention, for example inefficient discharging of the composition from a dosing means, applicator or reservoir (and so too the dose(s) of active ingredient) once the dosing means or applicator is actuated. Furthermore, a too low Tg may affect the disintegration and/or dissolution of compositions of the invention in the form of tablets for sublingual or peroral use.

In this respect, we prefer that the lowest measurable Tg of a composition of the invention is at least about 40° C., such as at least about 50° C., such as at least about including at least about 60° C., when measured at a relative humidity of up to about 35%, such as up to about 30%, including up to about 25% (e.g. up to about 20%, such as less than about 15%, e.g. less than about 10%). By 'lowest measurable Tg', we include that the composition of the invention may comprise particles that are heterogenous in their nature. In particular, particles may comprise discrete regions of the carrier materials, or composite mixtures thereof, and so may possess individual and separate Tg values. It will be clear to the skilled person that the value of the lowest measurable Tg has a strong impact on the physical stability of the composition.

We have found that compositions of the invention comprising a combination of a disaccharide and a polymer (e.g. HPMC as defined herein) and/or, particularly, a dextrin is capable of giving rise to an appropriate level of physical and chemical stability of compositions and active ingredients when compared to other carrier materials, when employed alone or in isolation.

A particularly preferred combination of carrier materials thus includes trehalose or, more preferably, a lactose, such as α-D-lactose monohydrate, and a dextrin, and especially a cyclodextrin, such as 2-hydroxypropyl-β-cyclodextrin, or a maltodextrin, such as maltodextrin 12DE. We have found that such a combination of carrier materials can be spray-dried together along with an active ingredient and also, if present, an alkyl saccharide in appropriate proportions to produce a composition of the invention that possesses both the desired physical and chemical stability under normal storage conditions, as defined herein.

We have found that relative amounts of the disaccharide and the polymer ingredients in the carrier material (and particularly so when the polymer is a dextrin) can be tailored to ensure the required level of physical and/or chemical stability of active ingredient whilst, at the same time, not lowering the Tg of the composition of the invention in such a manner that it affects its physical stability.

We have found that a ratio of between about 50:1 to about 1:50 of disaccharide:polymer (e.g. dextrin) by weight, based on the total weight of the composition, may work depending on the active ingredient that is employed. Preferred ratios are in the range of about 10:1 to about 1:40 (including up to about 1:30 or up to about 1:20), for example between about 2:1 and about 1:10, more preferably about 1:1 to about 1:8 of disaccharide:polymer (e.g. dextrin) by weight, based on the total weight of the composition.

Whatever their proportions in the final mixture, compositions of the invention include a spray-dried carrier material that comprises a combination of a disaccharide and a polymeric material (e.g. a dextrin). Thus, the carrier material may be prepared by spray drying those ingredients to form a composite carrier material either prior to spray-drying that carrier material along with the other essential ingredients to form a composition of the invention or, more preferably, is made in situ by spray-drying all of the essential components of the composition of the invention together.

Active pharmaceutical ingredients that may be employed in compositions of the invention include any compound that is pharmaceutically active.

Particular active pharmaceutical ingredients that may be mentioned include those that are suitable for transmucosal, including sublingual and, particularly, intranasal administration, for example at a dose of less than or equal to about 100 mg.

In this respect, compositions of the invention may comprise antipsychotic drugs (also referred to herein simply as 'antipsychotics'), including first-generation or second-generation antipsychotic drugs.

First-generation antipsychotics that may be employed in compositions of the invention include phenothiazines, such as acepromazine, chlorpromazine, cyamemazine, dixyrazine, fluphenazine, levomepromazine, mesoridazine, perazine, periciazine, perphenazine, pipotiazine, prochlorperazine, promazine, promethazine, prothipendyl, thioproperazine, thioridazine, trifluoperazine or triflupromazine; thioxanthenes, such as chlorprothixene, clopenthixol, flupentixol, thiothixene, zuclopenthixol; butyrophenones such as benperidol, bromperidol, droperidol, haloperidol, moperone, pipamperone or timiperone; dihydroindolone derivatives, such as dihydroindolon or molindolone; dibenzepine; diphenylbutylpiperidines, such as fluspirilene, penfluridol, or pimozide; dibenzothiazepines, such as tianepine or metiapine; perathiepine, chlorotepine, metitepine; tricyclics carpipramine, clocapramine, clorotepine, clotiapine, loxapine or mosapramine; molindone or substituted benzamides, such as sulpiride, sultopride, or veralipride.

Preferred phenorthiazines have a substituent at position 10, such as chlorpromazine, mesoridazine, pipotazine, perphenazine or trifluoperazine. Preferred substituents at position 10 are aliphatic hydrocarbons, piperidine or piperazine.

First-generation antipsychotics that may be employed in compositions of the invention include substances that block D2 receptors and/or block muscarin cholingeric receptors.

Preferred first-generation antipsychotics that may be employed in compositions of the invention block D2 receptors in the mesolimbic pathway and/or block muscarin cholingeric receptors, such as chlorpromazine, fluphenazine, haloperidol, perphenazine, thioridazine, thiothixene or trifluoperazine.

Second-generation antipsychotics that may be employed in compositions of the invention include benzamides, such as amisulpride, nemonapride, remoxipride sultopride, sulpiride or veralipride; benzisoxazoles/benzisothiazoles such as iloperidone, lurasidone, paliperidone, paliperidone palmitate, perospirone, risperidone or ziprasidone; butyrophenones, such as melperone; phenylpiperazines/quinolinones such as aripiprazole, brexpiprazole or cariprazine; tricyclics such as asenapine, clozapine, olanzapine, quetiapine or zotepine; blonanserin, pimavanserin, sertindole.

Second-generation antipsychotics that may be employed in compositions of the invention include serotonin-dopamine antagonists; substances that block or partially block serotonin 5-HT$_{2A}$ and/or 5-HT$_{1A}$ receptors and D$_2$ receptors simultaneously; substances showing an affinity for 5-HT$_{2A}$, D$_2$ and receptors of other systems, such as cholinergic, histaminergic, 5-HT$_{1A}$, 5-HT$_{2C}$ receptors and the like; substances that block D$_2$ and D$_3$ subtypes of the D$_2$-like receptors.

By 'D$_2$-like receptors', we mean the subfamily of dopamine receptors that bind the endogenous neurotransmitter dopamine comprising three G-protein coupled receptors that are coupled to G$_i$/G$_o$ and mediate inhibitory neurotransmission, of which include D$_2$, D$_3$, and D$_4$.

Optionally, antipsychotics that may be employed in compositions of the invention include partial dopamine receptor agonists comprising partial agonist at dopamine D$_2$ receptors acting as a functional antagonist in the mesolimbic dopamine pathway, but showing functional agonist activity in the mesocortical pathway.

Naturally-occurring antipsychotics, such as 1-stepholidine may also be employed in compositions of the invention.

Preferably, antipsychotics that act on the dopaminergic system only block the mesocortical pathway.

Substances that are D$_2$ antagonists may be employed in compositions of the invention. Preferably, these substances reduce dopaminergic neurotransmission in at least one of the four dopamine pathways. Dopamine pathways include the mesocortical pathway, the mesolimibic pathways, the nigrostriatal pathway and the tuberoinfundibular pathway. A preferred pathway is the mesolimbic pathway.

Preferred D$_2$ antagonists that may be employed in compositions of the invention include 3-PPP, aceprometazine, amisulpride, aripiprazole, BL-1020, blonanserin, buspirone, testosterone, chlorprothixene, desmethoxyfallypride, doxepin, eticlopride, fallypride, flunarizine, itopride, ketanserin, L-741,626, lumateperone, metoclopramide, ocaperidone, olanzapine, opipramol, panamesine, pimozide, pipamperone, pridopidine, raclopride, spiperone, stepholidine, tiotixene or trimethobenzamide Preferred second-generation antipsychotics that may be employed in compositions of the invention include aripiprazole, asenapine, clozapine, aloperidon, lurasidone, olanzapine, paliperidone, quetiapine, risperidone, cariprazine or ziprasidone.

More preferably, the composition of the invention comprises trifluoroperazine, haloperidol, prochlorperazine, blonanserin or, more preferably, loxapine or olanzapine.

Compositions of the invention may in the alternative comprise one or more anticonvulsant drugs, which drugs may include paraldehyde, stiripentol, potassium bromide, felbamate, valproic acid, sodium valproate, divalproex sodium, vigabatrin, progabide, tiagabine, topiramate, hydantoins (such as ethotoin, phenytoin, mephenytoin and fosphenytoin), paramethadione, trimethadione, ethadione, beclamide, primidone, brivaracetam, etiracetam, levetiracetam, seletracetam, ethosuximide, phensuximide, mesuximide, acetazolamide, sultiame, methazolamide, zonisamide, lamotrigine, pheneturide, phenacemide, valpromide, valnoctamide, perampanel, stiripentol, pyridoxine. Preferred anticonvulsant drugs include barbiturates (e.g. amobarbital, methohexital, thiamylal, thiopental, phenobarbital, primidone, methylphenobarbital (mephobarbital) and barbexaclone), as well as benzodiazepines (e.g. clorazepate, diazepam, flurazepam, halazepam, prazepam, chlordiazepoxide, lormetazepam, oxazepam, temazepam, clonazepam, flunitrazepam, nimetazepam, nitrazepam, adinazolam, alprazolam, estazolam, triazolam, climazolam, loprazolam, midazolam, bentazepam, clotiazepam, etizolam, metizolam, deschloroetizolam and, especially, lorazepam), and also carboxam ides (e.g. oxcarbazepine, eslicarbazepine and, particularly, carbamazepine).

Compositions of the invention may also comprise one or more cannabinoid drug. The term 'cannabinoid' refers to a compound that acts on cannabinoid receptors in cells that alter neurotransmitter release in the brain. Ligands for these receptor proteins include the endocannabinoids (produced naturally in the body by animals), the phytocannabinoids (found in cannabis and some other plants), and synthetic cannabinoids (manufactured artificially).

The most notable cannabinoid is the phytocannabinoid tetrahydrocannabinol (THC), the primary psychoactive compound in cannabis. There are at least 113 different cannabinoids isolated from cannabis plant, exhibiting varied effects.

In specific embodiments, the cannabinoid is a cannabinoidergic (or cannabinergic), i.e. a compound that acts on endocannabinoid neurotransmitters (e.g., cannabinoid receptor agonist, cannabinoid receptor antagonist, endocannabinoid enhancer (eCBE), or endocannabinoid reuptake inhibitor (eCBRI)).

Cannabinoids that may be employed in compositions and/or dosage forms of the invention include phytocannabinoids (e.g., CBG, CBC, CBD, THC, CBN, CBE, iso-THC, CBL, and CBT) and endocannabinoids (e.g., AEA, 2-AG, noladin ether, NAD A, OAE, and LPI). The cannabinoid may be a plant cannabinoid (e.g., cannabigerol-type (CBG-type), cannabichromene-type (CBC-type), cannabidiol-type (CBD-type), cannabinodiol-type (CBND-type), $\Delta^9$-tetrahydrocannabinol-type ($\Delta^9$-THC-type), $\Delta^8$-tetrahydrocannabinol-type ($\Delta^8$-THC-type), cannabinol-type (CBN-type), cannabitriol-type (CBT-type), cannabielsoin-type (CBE-type), isocannabinoids, cannabicyclol-type (CBL-type), cannabitriol-type (CBT-type), or cannabichromanone-type (CBCN-type)). Further plant cannabinoid that may be employed in compositions and/or dosage forms of the invention include dehydrocannabifuran, cannabifuran, cannabichromanon, 10-oxo-δ-6a-tetrahydrocannabinol or cannabiripsol.

Alternatively, the cannabinoid may be a synthetic cannabinoid (e.g., nabilone, rimonabant, JWH-018, JWH-073, CP-55940, dimethylheptylpyran, HU-210, HU-331, SR144528, WIN 55,212-2, JWH-133, levonantradol (Nantrodolum), or AM-2201) and mimics thereof.

The cannabinoid may include at least one of THC (tetrahydrocannabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), CBT (cannabicitran), Nabilone, Rimonabant, JWH-018, JWH-073, CP-55940, Dimethylheptylpyran, HU-210, HU-331, SR144528, WIN 55,212-2, JWH-133, Levonantradol (Nantrodolum), or AM-2201.

Preferred endocannabinoids are endogenous lipid-based retrograde neurotransmitters that bind to cannabinoid receptors, such as $CB_1$, $CB_2$, or $CB_3$ (GPR55) and cannabinoid receptor proteins that are expressed throughout the vertebrate central nervous system (including the brain) and peripheral nervous system.

Preferred cannabinoids include THC (tetrahydrocannabinol, e.g. dronabinol), THCA (tetrahydrocannabinolic acid), CBD (cannabidiol), CBDA (cannabidiolic acid), CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethyl ether), CBE (cannabielsoin), and CBT (cannabicitran). A particularly preferred cannabinoid is cannabidiol.

Compositions of the invention may also comprise peptides. Peptides that may be employed include naturally occurring peptides or their synthetic analogues, semi-synthetic peptides, synthetic peptides, proteoses.

The peptide may be a single chain peptide or a multichain peptide, i.e. a peptide formed from two or more distinct amino acid chains, such as human insulin, or a cyclic peptide, such as cyclosporin. It is preferred that the peptide is not a naturally-occurring or a recombinant protein.

Types of naturally occurring peptides include plant peptides, bacterial/antibiotic peptides, fungal peptides, invertebrate peptides, amphibian/skin peptides, venom peptides, cancer/anticancer peptides, vaccine peptides, immune/inflammatory peptides, brain peptides, endocrine peptides, ingestive peptides, gastrointestinal peptides, cardiovascular peptides, renal peptides, respiratory peptides, opiate peptides, neurotrophic peptides, blood-brain peptides, ribosomal peptides, non-ribosomal peptides, neuropeptides, lipopeptides, and peptide hormones.

By 'proteoses' we mean mixtures of peptides produced by the hydrolysis of proteins.

Peptides that may be employed in compositions of the invention may be naturally occurring peptides, such as insulin, interferon β, interferon γ, TPA, albumin, HGH, factor VIII, erythropoietin, calcitonin, oxytocin or vasopressin or their synthetic analogues, semi-synthetic peptides, such as voclosporin or synthetic peptides.

Semi-synthetic peptides may be obtained by chemically treating natural source peptides.

Peptides that may be employed in compositions of the invention may be ribosomal peptides including antimicrobial peptides, such as peptides belonging to the magainin family, the cecropin family, the cathelicidin family, defensin family; tachykinin peptides, such as substance P, kassinin, neurokinin A, eledoisin, neurokinin B; vasoactive intestinal peptides, such as VIP (Vasoactive Intestinal Peptide; PHM27), PACAP (Pituitary Adenylate Cyclase Activating Peptide), peptide PHI 27 (Peptide Histidine Isoleucine 27), GHRH 1-24 (Growth Hormone Releasing Hormone 1-24). Glucagon, secretin; pancreatic polypeptide-related peptides, such as NPY (NeuroPeptide Y), PYY (Peptide YY), APP (Avian Pancreatic Polypeptide), PPY Pancreatic Polypeptide; opioid peptides, such as proopiomelanocortin (POMC) peptides, endomorphins (and analogues such as endomorphin-2), enkephalin pentapeptides, prodynorphin peptides; calcitonin peptides, such as calcitonin, amylin, AGG01 or self-assembling peptide, such as amphiphilic peptides, aromatic short peptides or biomimetic peptides.

Preferably, ribosomal peptides have hormonal activity.

Peptides that may be employed in compositions of the invention include B-type natriuretic peptide (BNP) lactotripeptides, peptidic components from traditional Chinese medicine Colla Corii Asini.

Peptides that may be employed also include peptides that acts as GnRH agonists, such as buserelin, gonadorelin, goserelin, histrelin, leuprorelin, nafarelin, triptorelin, and GnRH antagonists, such as abarelix, cetrorelix, degarelix, ganirelix, elagolix, relugolix and teverelix; peptides acting as vasopressin receptor 2 (AVPR2) agonist, such as desmopressin, or as GLP-1 receptor agonist, such as liraglutide, exenatide, lixisenatide, albiglutide, dulaglutide or semaglutide Peptides may include those that act as SRIF agonists, such as somatostatin and analogues, such as octreotide, pasireotide or lanreotide.

Peptides that may be employed in the composition of the invention further include peptides that may be used to treat osteoporosis, such as teriparatide (a recombinant protein form of parathyroid hormone).

Other peptides that may be employed include immunosuppressant peptides that may be used to treat rheumatoid arthritis, psoriasis, Crohn's disease, nephrotic syndrome and/or to prevent tissue/organ transplant rejection, such as cyclosporin.

Preferably, the compositions of the invention comprising a peptide comprise one or more of buserelin, gonadorelin, goserelin, histrelin, leuprorelin, nafarelin, triptorelin, abarelix, cetrorelix, degarelix, ganirelix, elagolix, relugolix, teverelix, leuprolide, liraglutide, octreotide and desmopressin.

Compositions of the invention may comprise bisphosphonates, such as alendronate, clodronate, etidronate, ibandronate, neridronate, olpadronate, pamidronate, risedronate, tiludronate and zoledronate.

Compositions of the invention may comprise general anaesthetics and/or sedatives. General anaesthetics and/or sedatives that may be used in compositions of the invention include those that are normally administered intravenously, such as barbiturates (e.g. amobarbital, methohexital, thiamylal and thiopental); benzodiazepines (such as any of those mentioned hereinbefore under the anti-convulsant heading and particularly diazepam, lorazepam and midazolam); and other drugs, such as etomidate, propofol and particularly, ketamine.

Other sedative agents include muscle relaxants, such as succinylcholine, decamethonium, mivacurium, rapacuronium, atracurium, cisatracurium, rocuronium, vecuronium, alcuronium, doxacurium, gallamine, metocurine, pancuronium, pipecuronium and tubocurarine.

Compositions of the invention may comprise analgesics, including non-steroidal antiflammatory drugs, such as aspirin, diflunisal, ibuprofen, dexibuprofen, naproxen, fenoprofen, ketoprofen, dexketoprofen, flurbiprofen, oxaprozin, loxoprofen, indomethacin, tolmetin, sulindac, etodolac, ketorolac, diclofenac, aceclofenac, bromfenac, nabumetone, piroxicam, meloxicam, tenoxicam, droxicam, lornoxicam, isoxicam, phenylbutazone (bute), mefenamic acid, meclofenamic acid, flufenamic acid, tolfenamic acid, celecoxib, rofecoxib, valdecoxib, parecoxib, lumiracoxib, etoricoxib, firocoxib, nimesulide, clonixin and licofelone; and synthetic opioid analgesics, such as tramadol, alfentanil, fentanyl, remifentanil and sufentanil. Preferred analgesics include aspirin, as well as ketorolac and diclofenac, in addition piroxicam, meloxicam, tenoxicam, droxicam, lornoxicam and isoxicam.

Compositions of the invention may comprise antidepressants, including selective serotonin reuptake inhibitors (SSRIs), such as fluoxetine, sertraline, doxepin, citalopram, escitalopram, fluvoxamine, paroxetine; serotonin-norepinephrine reuptake inhibitors (SNRIs), such as desvenlafaxine, duloxetine, levomilnacipran, milnacipran and venlafaxinel serotonin modulator and stimulators (SMSs), such as vilazodone and vortioxetine; serotonin antagonist and reuptake inhibitors (SARIs), such as nefazodone and trazodone; norepinephrine reuptake inhibitors (NRIs), such as atomoxetine, reboxetine, teniloxazine and viloxazine; norepinephrine-dopamine reuptake inhibitors (NDRIs), such as bupropion; tricyclic antidepressants, such as amitriptyline, amitriptylinoxide, clomipramine, desipramine, dibenzepin, dimetacrine, dosulepin, doxepin, imipramine, lofepramine, melitracen, nitroxazepine, nortriptyline, noxiptiline, opipramol, pipofezine, protriptyline and trimipramine; tetracyclic antidepressants, such as amoxapine, maprotiline, mianserin, mirtazapine and setiptiline; monoamine oxidase inhibitors (MAOIs), such as isocarboxazid, phenelzine, tranylcypromine, selegiline, caroxazone, metralindole, moclobemide, pirlindole, toloxatone and bifemelane; and others, such as agomelatine, tandospirone, tianeptine and, more preferably, brexanolone, esketamine and ketamine.

Compositions of the invention may comprise antihistamines (i.e. $H_1$ antagonists/inverse agonists), such as acrivastine, azatadine, azelastine, bilastine, bromodiphenydramine, brompheniramine, buclizine, carbinoxamine, cetirizine, chlorodiphenhydramine, chlorpheniramine, clemastine, cyclizine, cyproheptadine, desloratadine, dexbrompheniramine, dexchlorpheniramine, dimenhydrinate, dimetindene, diphenhydramine, doxylamine, ebastine, embramine, fexofenadine, hydroxyzine, levocabastine, levocetirizine, loratadine, meclizine, mirtazapine, olopatadine, orphenadrine, phenindamine, pheniramine, phenyltoloxamine, promethazine, pyrilamine, quetiapine, rupatadine, alergoliber, tripelennamine and triprolidine.

Compositions of the invention may comprise modulators of neurotransmitter receptors (other than those already mentioned hereinbefore or hereinafter), including modulators of adrenergic receptors (including the $\alpha_{1A}$, $\alpha_{1b}$, $\alpha_{1c}$, $\alpha_{1d}$, $\alpha_{2a}$, $\alpha_{2b}$, $\alpha_{2c}$, $\alpha_{2d}$, $\beta_1$, $\beta_2$, $\beta_3$ sub-receptors), GABAergic receptors (including the $GABA_A$, $GABA_{B1a}$, $GABA_{B1b}$, $GABA_{B2}$, $GABA_C$ sub-receptors), dopamine receptors (including the $D_1$, $D_2$, $D_3$, $D_4$, and $D_5$ sub-receptors), glutaminergic receptors (including the NMDA, AMPA, kainate, $mGluR_1$, $mGluR_2$, $mGluR_3$, $mGluR_4$, $mGluR_5$, $mGluR_6$, $mGluR_7$), cholinergic receptors (including muscarinic (M1, M2, M3, M4 and/or M5) receptors, nicotinic receptors, muscle receptors and neuronal ($\alpha$-bungarotoxin-insensitive) and $\alpha$-bungarotoxin-sensitive) receptors), serotonergic receptors (including the $5\text{-HT}_{1A}$, $5\text{-HT}_{1B}$, $5\text{-H}_{1D}$, $5\text{-H}_{1E}$, $5\text{-H}_{1F}$, $5\text{-HT}_{2A}$, $5\text{-HT}_{2B}$, $5\text{-HT}_{2C}$, $5\text{-HT}_3$, $5\text{-HT}_4$, $5\text{-HT}_5$, $5\text{-H}_6$, $5\text{-H}_7$ sub-receptors), and glycinergic receptors.

Modulators of glutaminergic receptors that may be mentioned, and which are not already mentioned hereinbefore or hereinafter, include selfotel, aspartame, amantadine, agmatine, dextromethorphan, eliprodil, remacemide, gabapentin and the like. Modulators of GABAergic receptors that may be mentioned include short-acting hypnotics, such as zaleplon, zolpidem, eszopiclone or zopiclone. Modulators of adrenergic receptors that may be mentioned include norepinephrine, isoprenaline and, more particularly, epinephrine (adrenaline). Modulators of dopaminergic receptors that may be mentioned, and which are not already mentioned hereinbefore or hereinafter, include cabergoline, bromocriptine, pram ipexole, pergolide, ropinirole, rotigotine and particularly, apomorphine. Modulators of serotonergic receptors that may be mentioned, and which are not already mentioned hereinbefore, include the triptans (such as almotriptan, eletriptan or, alternatively, rizatriptan, zolmitriptan, sumatriptan, frovatriptan and naratriptan).

Other antimigraine compounds that may be mentioned include diltiazem, lisuride, verapamil, ergotamine, dihydroergotamine, caffeine, etc.

Further active ingredients that may be used in compositions of the invention include cardiovascular drugs, including the following:

anticoagulants, such as Factor Xa inhibitors (including apixaban, dabigatranetexilat, edoxaban and rivaroxaban); and platelet inhibitors (including clopidogrel, ticlopidin, aspirin, dipyridamole, epoprostenol, iloprost, abciximab, eptifibatid, tirofiban, treprostinil, prasugrel, cilostazol, ticagrelor, cangrelor, vorapaxar and selexipag);

α- and β-adrenoreceptor antagonists (i.e. α- and β-blockers), which are used to treat a variety of cardiovascular disorders (such as hypertension, high blood pressure, etc.). α-blockers include prazosin and doxazosin, β-blockers include atenolol, pindolol, propranolol, metoprolol, as well as timolol, sotalol, nadolol, carteolol, penbutolol, acebutolol, betaxolol, bisoprolol, esmolol, nebivolol, landiolol, etc.; and combined α- and β-blockers include labetalol and carvedilol;

angiotensin-converting enzyme (ACE) inhibitors, such as captopril, enalapril, lisinopril, perindopril, ramipril, benazepril, fosinopril, trandolapril, spirapril and moexipril;

angiotensin II receptor antagonists, such as losartan, eprosartan, valsartan, irbesartan, candesartan, telmisartan, olmesartan medoxomil, azilsartan and medoxomil;

neprilysin inhibitors, such as sacubitril;

calcium channel blockers, such as amlodipine, felodipine, isradipine, nifedipine, nimodipine, nisoldipine, clevidipine, verapamil, diltiazem and bepridil;

diuretics, such as bendroflumethiazide, hydrochlorothiazide, hydroflumethiazide, chlorothiazide, polythiazide, chlorthalidone, metolazone, indapamide, furosemide, bumetanide, torsemide, spironolactone, eplerenone, amiloride, triamterene, tolvaptan and conivaptan;

HMG-CoA reductase inhibitors (cholesterol-lowering medications), such as simvastatin, lovastatin, pravastatin, fluvastatin, atorvastatin, rosuvastatin and pitavastatin;

vasodilators, such as nitroglycerin, isosorbide and isosorbide mononitrate;

endothelin receptor antagonists, such as bosentan, ambrisentan, sitaxentan, macitentan and riociguat.

digitalis preparations, i.e. drug preparations that contain cardiac glycosides, such as digoxin; and other hypertension treatments, such as hydralazine, veratrum, pargyline, etc.

Other active ingredients that may be used in compositions of the invention include antiviral agents against e.g. hepatitis C (such as ribavirin, sofosbuvir, dasabuvir, elbasvir, grazoprevir, ledipasvir, ombitasvir, paritaprevir, ritonavir, velpatasvir, voxilaprevir, glecaprevir and pibrentasvir); more particularly drugs that are useful in the treatment of erectile dysfunction, such as avanafil, sildenafil, tadalafil, vardenafil, etc.; muscle relaxants, such as quinine, chlorzoxaone, etc.; stimulants, such as ephedrine, fenfluramine, caffeine, amphetamine, methamphetamine, dexamphetamine, methcathinone, etc.; antiemetics, such as dolasetron, granisetron, metoclopramide, meclizine, cyclizine, ondansetron, palonosetron, dimenhydrinate, diphenhydramine, scopolamine, promethazine, etc; and other drugs, including chlordiazepoxide, betahistine, clonidine, hyoscyamine and sex hormones (e.g. testosterone, estrogen, estradiol, etc.).

The skilled person will appreciate that one or more of the aforementioned active ingredients may have one or more of the aforementioned medical functions. For example, ketamine may have biological activities that include analgesic, sedative and antidepressant functions.

Preferred active ingredients that may be employed in compositions of the invention include those (listed above or otherwise) that comprise a molecular structure that includes at least one nitrogen atom in the form of an amine moiety. The amine moiety may be a quaternary amine or, more preferably, may be a primary, a secondary or a tertiary amine.

Such amine moieties may be aromatic in their nature, that is to say amine moieties wherein one or more carbon atoms is/are bound to the at least one nitrogen atom within the active ingredient's molecular structure is sp2 hybridized (i.e. comprises one or more 'aryl' groups). More preferably however, such amine moieties may be aliphatic in their nature, that is to say amine moieties wherein one or more carbon atoms is/are bound to the at least one nitrogen atom within the active ingredient's molecular structure is sp3 hybridized (i.e. comprises one or more 'alkyl' groups).

Drugs that comprise amine groups include many of those mentioned herein, such as those that mimic or to interfere with the action of natural amine neurotransmitters, for example chlorpheniramine, chlorpromazine, ephedrine, phenylephrine, amitriptyline, imipramine, lofepramine, clomipramine, nortriptyline, desipramine, amoxapine, and especially, loxapine, ketamine, apomorphine, epinephrine, olanzapine, aripiprazole, haloperidol, ziprasidone, asenapine, risperidone, and any of the aforementioned triptans.

In addition, and/or in the alternative, preferred active ingredients that may be employed in compositions of the invention include those (whether listed above (e.g. in the list of amine drugs) or otherwise) with a pKa that is at least about 0, such as at least about 2, including at least about 4, more particularly at least about 6, e.g. at least about 7.5, for example at least about 8 and especially at least about 8.5; as well as no more than about 14, such as no more than about 12.5, including no more than about 12, preferably no more than about 11.5, such as no more than about 11, including no more than about and especially no more than about 10.

Further in addition, and/or in the alternative, preferred active ingredients that may be employed in compositions of the invention include those (listed above or otherwise) with an aqueous solubility that is at least about 10 mg/mL, such as at least about 1 mg/mL. including at least about 100 μg/mL, such as at least about 10 μg/mL, for example at least about 1 μg/mL and, particularly, at least about 0.5 μg/mL at room temperature and atmospheric pressure. 'Aqueous' solubility will be understood to include not only solubility in pure water, but also in relevant physiological fluids, and especially those found in the nose (which can also be simulated in terms of isotonicity and pH).

It is preferred that the active ingredient that is employed the composition of the invention is not an opioid antagonist. In particular, when the composition of the invention is formulated for (and/or is suitable for) intranasal administration, it is preferred that the active ingredient that is employed therein is not an opioid antagonist.

According to further aspects of the invention, there is provided a composition of the invention that is suitable for and/or formulated to delivery of the one or more pharmaceutically-active ingredients that are included therein:

perorally to the gastrointestinal tract;

topically to the ocular, vaginal, cervical and/or anorectal mucosae;

sublingually (e.g. as a tablet or as a powder);

buccally (e.g. as a buccal tablet or patch);

by injection or by infusion (e.g. as a suspension of as an infusion); or intranasally as a powder, provided that, in the latter (intranasal) case, one or more of said pharmaceutically-active ingredients is not an opioid antagonist.

Additionally, there are provided methods of treatment of a patient, which methods comprise administration of a composition of the invention by an administration route that includes:

perorally to the gastrointestinal tract;

topically to the ocular, vaginal, cervical and/or anorectal mucosae;

sublingually (e.g. as a tablet or as a powder);

buccally (e.g. as a buccal tablet or patch);

by injection or by infusion (e.g. as a suspension of as an infusion); or intranasally as a powder, which composition comprises one or more pharmaceutically-active ingredients that is suitable for and/or intended for delivery by one or more of the above-mentioned administration routes, provided that, in the latter (intranasal) case, one or more of said pharmaceutically-active ingredients is not an opioid antagonist.

The term 'opioid antagonist' includes any agent that has little to no opioid activity, but is capable of displacement of an opioid agonist from an opioid receptor, so reversing or preventing the pharmacological effects of an opioid agonist, whether such effects are intended (euphoria, sedation and/or reduction in cravings), or unintended (unconsciousness, depressed heart rate, depressed lung function, hypoxia, etc.). Opioid antagonists are therefore of potential use in the treatment of substance (such as opioid, including opiate) overdose. In this respect, the term 'opioid agonists' include exogenous opioid receptor ligands (i.e. those mentioned hereinbefore) and endogenous opioid receptor ligands (e.g. endorphins). Opioid antagonists thus include naloxone, nalmefene and naltrexone, or pharmacologically-acceptable salts thereof, such as their hydrochloride salts. In the context of the present application, the term 'opioid antagonist' also includes active pharmaceutical ingredients that are known to be partial antagonists of opioid receptors, such as buprenorphine, and active pharmaceutical ingredients that are otherwise known to be useful in the treatment of opioid withdrawal symptoms, such as lofexidine.

Preferred active ingredients that may be employed in compositions of the invention include one or more of the GnRH agonists or one or more of the GnRH antagonists mentioned hereinbefore, in addition to lurasidone, blonanserin, olanzapine, carbamazepine, lorazepam and cannabidiol, particularly aspirin and, more particularly, ketorolac, as well as, aripiprazole, haloperidol, ziprasidone, asenapine, loxapine, ketamine, apomorphine, epinephrine, almotriptan or eletriptan or, alternatively, rizatriptan, zolmitriptan, sumatriptan, frovatriptan and naratriptan.

Combinations of one or more of the aforementioned active ingredients in the same, or in different classes may be employed.

The active ingredients mentioned above may be provided in the form of a (e.g. pharmaceutically-acceptable) salt, including any such salts that are known in the art and described for the drugs in question to in the medical literature, such as *Martindale—The Complete Drug Reference, 38th* Edition, Pharmaceutical Press, London (2014) and the documents referred to therein (the relevant disclosures in all of which documents are hereby incorporated by reference).

Otherwise, pharmaceutically acceptable salts include acid addition salts and base addition salts, which salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared using techniques known to those skilled in the art, such as by exchanging a counter-ion of a compound of the invention in the form of a salt with another counter-ion, for example using a suitable ion exchange resin.

Particular acid addition salts that may be mentioned include carboxylate salts, such as succinate, tartrate, formate, acetate, benzoate, oxalate, fumarate, maleate and the like, sulfonate salts, such as methanesulfonate, ethanesulfonate, toluenesulfonate and the like, halide salts, such as hydrochloride, hydrobromide and the like, sulfate and phosphate salts, such as sulfate or phosphate and the like.

Particular base addition salts that may be mentioned include salts formed with alkali metals (such as Li, Na and K salts), alkaline earth metals (such as Mg and Ca salts), or other metals (such as Al and Zn salts) amine bases (such as ammonia, ethylenediamine, ethanolamine, diethanolamine, triethanolamine, tromethamine). More particularly, base addition salts that may be mentioned include Mg, Ca and, most particularly, K and Na salts.

When compositions of the invention are made by a solvent-based process, as described hereinbefore, including by way of a process of spray-drying, this may result in the presence of active ingredient in a form in which it is no longer in the form of a crystalline salt because it is freely dispersed within, and encapsulated by, the carrier materials in an amorphous form. However, despite not being in the form of a crystalline salt, which it would normally be in the case of a typical solid state mixture and/or powder composition, compositions of the invention may provide for little to no loss in chemical stability of that active ingredient under the normal storage conditions mentioned herein.

The amount of active ingredient that may be employed in a single dose of a composition of the invention must be sufficient so exert its pharmacological effect. For transmucosally- (e.g. sublingually-, buccally- and, particularly, intranasally-) administered compositions of the invention, that amount must not exceed about 100 mg in a single dose. Actual doses of the relevant active ingredients mentioned above include those that are known in the art and described for the drugs in question to in the medical literature, such as *Martindale—The Complete Drug Reference, 38th* Edition, Pharmaceutical Press, London (2014) and the documents referred to therein, the relevant disclosures in all of which documents are hereby incorporated by reference. However, compositions of the invention may be found to exhibit good bioavailability and/or rapid absorption, resulting in a more rapid onset of action and/or higher plasma concentrations, compared to prior art compositions comprising the same active ingredient.

Compositions of the invention may be found in this respect to exhibit surprisingly good bioavailability and speed of absorption compared to corresponding compositions that do not include, for example, alkyl saccharides, and/or include different excipients that are known to act as surfactants.

In this respect, pharmacologically-appropriate amounts of active ingredients in compositions of the invention may be less than those referred to in the literature (vide supra). Such amounts may nevertheless be determined by the skilled person and may vary with the type and severity of the condition that is to be treated, and what will be most suitable for an individual patient. This is also likely to vary with the nature of the formulation, as well as the type and severity of the condition that is to be treated, as well as the age, weight, sex, renal function, hepatic function and response of the particular patient to be treated.

Depending upon the potency of the active ingredient, and upon the final dosage form that is to be employed, the total amount of active ingredient that may be employed in a composition of the invention may be in the range of about 0.0002%, for example about 0.001%, such as about 0.01%, including about 0.1%, (e.g. about 1%, about 2% or about 5%), such as about 10% (e.g. about 20%) up to about 95%, such as about 75%, for example about 50%, e.g. about 40%, by weight based upon the total weight of the composition. This is independent of the number of separate doses of composition (which should be the same) that are initially present in the dosing means of the invention.

For transmucosal, including buccal, sublingual or, preferably, intranasal, administration, appropriate doses of active ingredients (calculated as the free acid/base) per unit dosage are in the range of about 1 μg to about 100 mg (e.g. about 80 mg), such as between about 1 mg and about 60 mg (e.g. about 3 mg, such as about 10 mg to about 50 mg), depending on the active ingredient that is employed.

For certain, specific active ingredients mentioned hereinbefore, when administered transmucosally, including buccally, sublingually or, preferably, intranasally, specific doses that may be employed in compositions of the invention (in each case calculated as the free (acid/base) compound) include, for lurasidone, about 10 to about 100 mg; for blonanserin, about 2 to about 10 mg; for olanzapine, about 5 to about 20 mg; for carbamazepine, about 10 to about 100 mg; for lorazepam, about 0.5 to about 4 mg; for cannabidiol, about 10 to about 100 mg, for loxapine, about 5 mg to about 50 mg, (e.g. about 7 to about 12 mg, such as about 10 mg); for apomorphine, about 1 mg to about 10 mg; for ketorolac, about 10 mg to about 40 mg; for aripiprazole, about 1 mg to about 30 mg; for haloperidol, about 1 mg to about 10 mg (such as about 2 mg to about 5 mg); for ziprasidone, about 10 to about 100 mg; for asenapine, about 2.5 mg to about 20 mg (e.g. about 5 and about 10 mg); for epinephrine, about 0.1 mg to about 5 mg (e.g. about 1 mg); for almotriptan, about 10 mg to about 50 mg (e.g. about 12.5 mg to about 40 mg); for eletriptan, about (oral dose 30 mg to about 60 mg (e.g. about 40 mg); for sumatriptan, about 5 mg to about 15 mg (e.g. about 11 mg); for zolmitriptan, about 1 mg to about 10 mg, such as about 2 mg to about 7.5 mg (e.g. about 2.5 mg and about 5 mg). In addition, for aspirin, suitable specific transmucosal (e.g. buccal, sublingual or, preferably, intranasal) doses that may be employed in compositions of the invention (calculated as the free acid compound) are in the range of about 5 to about 100 mg.

For other forms of administration (e.g. administration by injection or perorally), appropriate doses of active ingredients (calculated as the free acid/base) per unit dosage are in the range of about 1 μg to about 500 mg (e.g. about 400 mg), such as between about 1 mg and about 300 mg (e.g. about 3 mg, such as about 10 mg to about 200 mg), depending on the active ingredient that is employed.

For the active ingredients mentioned above, when administered via routes that are other than transmucosal, specific doses that may be employed in compositions of the invention (in each case calculated as the free (acid/base) compound) include, for lurasidone, about 10 to about 100 mg; for blonanserin, about 2 to about 10 mg; for olanzapine, about 5 to about 20 mg; for carbamazepine, about 10 to about 100 mg; for lorazepam, about 0.5 to about 4 mg; for cannabidiol, about 10 to about 100 mg, for loxapine, about 5 mg to about 50 mg, (e.g. about 7 to about 12 mg, such as about 10 mg); for apomorphine, about 1 mg to about 10 mg; for ketorolac, about 10 mg to about 40 mg; for aripiprazole, about 1 mg to about 30 mg; for haloperidol, about 1 mg to about 10 mg (such as about 2 mg to about 5 mg); for ziprasidone, about 10 to about 100 mg; for asenapine, about 2.5 mg to about 20 mg (e.g. about 5 and about 10 mg); for epinephrine, about 0.1 mg to about 5 mg (e.g. about 1 mg); for almotriptan, about 10 mg to about 50 mg (e.g. about 12.5 mg to about 40 mg); for eletriptan, about (oral dose 30 mg to about 60 mg (e.g. about 40 mg); for sumatriptan, about 5 mg to about 15 mg (e.g. about 11 mg); for zolmitriptan, about 1 mg to about 10 mg, such as about 2 mg to about 7.5 mg (e.g. about 2.5 mg and about 5 mg); and for aspirin, about 5 to about 500 mg, such as about 10 mg to about 300 mg.

According to three further aspects of the invention there is provided:
a composition of the invention for use in the treatment of a condition for which the at least one pharmaceutically-active compound that is/are included therein is/are useful for (for example by transmucosal, such as intranasal, administration of said composition);
the use of a composition of the invention for the manufacture of an (e.g. transmucosal, such as an intranasal) medicament for the treatment of a condition for which the at least one pharmaceutically-active compound that is/are included therein is/are useful for; and
a method of treatment of a condition for which the at least one pharmaceutically-active compound that is/are included within composition of the invention is/are useful for, which method comprises the (e.g. transmucosal, such as intranasal) administration of a composition of the invention to a patient suffering from, or susceptible to, said condition.

In this regard, compositions of the invention comprising antipsychotic drugs, such as those mentioned hereinbefore are useful in the treatment of psychosis. There is thus provided a composition of the invention comprising at least one antipsychotic drug for use in the treatment of psychosis.

Psychosis will be understood to include a wide range of clinical psychotic conditions, including mood disorders, such as schizophrenia; schizoaffective disorder; bipolar disorder; agitation associated with schizophrenia and/or bipolar disorder; depression (e.g. severe depression) and/or anxiety; obsessive-compulsive disorder (OCD) and/or attention deficit hyperactivity disorder (ADHD); physical problems, such as hiccups, problems with balance and nausea; or agitation and psychotic experiences in dementia. Preferred conditions include schizophrenia and schizoaffective disorder and symptoms thereof (e.g. delusions and hallucinations), bipolar disorder and symptoms thereof (e.g. depression and mania) and OCD/ADHD.

Antipsychotic drugs that are useful in the treatment of schizophrenia and schizoaffective disorder include first-generation antipsychotics, such as chlorpromazine, fluphenazine, haloperidol, perphenazine, thioridazine, thiothixene or trifluoperazine; second-generation antipsychotics, such as aripiprazole, asenapine, cariprazine, clozapine, olanzapine, paliperidone, paliperidone palmitate, quetiapine, risperidone, ziprasidone, blonanserin, lurasidone and, particularly, loxapine). There is thus provided a composition of the invention comprising one or more of the foregoing antipsychotic drugs, and particularly, blonanserin, lurasidone, olanzapine and, more particularly, loxapine for use in the treatment of schizophrenia. Carbamazepine may also be used to treat schizophrenia.

Antipsychotic drugs that are useful in the treatment of bipolar disorder include aripiprazole, asenapine, cariprazine, clozapine, olanzapine, quetiapine, risperidone, ziprasidone and, particularly, lurasidone. Carbamazepine may also be used to treat bipolar disorder.

Antipsychotic drugs that are useful in the treatment of ADHD include quetiapine, risperidone and, particularly, olanzapine. There is thus provided a composition of the invention comprising one or more of quetiapine, risperidone and, particularly, olanzapine for use in the treatment of ADHD.

Antipsychotic drugs that are useful in the treatment of agitation associated with schizophrenia and/or bipolar disorder include loxapine, olanzapine, aripiprazole, haloperidol, ziprasidone and asenapine.

Anticonvulsant drugs, such as any of the benzodiazepines mentioned hereinbefore (e.g. lorazepam) and carboxamides (e.g. carbamazepine), and specific cannabinoid drugs, such as cannabidiol, may be used to treat seizure disorders, including epilepsy, status epilepticus and the like.

Benzodiazepines (e.g. lorazepam) may also be useful as sedatives and/or in the treatment of anxiety disorders.

Compositions of the invention that comprise peptides such as those mentioned hereinbefore are useful, depending on the peptide(s) that is/are included in such a composition, in the treatment of a wide range of clinical conditions including diabetes mellitus, diabetes insipidus, obesity, bedwetting, haemophilia A, von Willebrand disease, high blood urea levels, night time urination, bleeding disorders, prostate cancer, breast cancer, polycystic disease, hypotension, diarrhoea, endometriosis or uterine fibroids.

Examples of a polycystic disease include polycystic kidney disease, polycystic liver disease or polycystic ovarian syndrome. Hypotension includes orthostatic hypotension and postprandial hypotension. Diarrhoea may include intractable diarrhoea, also termed refractory diarrhoea. The diarrhoea may also be secretory diarrhoea, which may be chronic; may be caused by dumping syndrome, by short bowel syndrome, by chemotherapy, by radiotherapy, by HIV/AIDS and/or by a neuroendocrine tumor (e.g. a carcinoid tumour or a Vasoactive Intestinal Peptide (VIP) secreting adenoma), or be due to graft-versus-host disease, irritable bowel syndrome (IBS), inflammatory bowel disease (which includes conditions that cause the gut to become inflamed, such as Crohn's disease and ulcerative colitis), coeliac disease (also termed celiac sprue), chronic pancreatitis, diverticular disease, endocrine disorders, vasculitis, post-surgical diarrhoea, carbohydrate malabsorption syndrome, amyloidosis, lactose intolerance, small bowel bacterial overgrowth, hepatobiliary disorders, inadequate luminal bile acid, bile acid malabsorption, loss of regulated gastric emptying, pancreatic exocrine insufficiency or neoplasia e.g. bowel cancer or may be due to invasive infectious disease and/or bacterial endotoxins e.g. cholera.

Peptides that may be employed in compositions of the invention for use in the treatment of hormone-responsive cancers, such as prostate cancer or breast cancer, and estrogen-dependent conditions such as endometriosis or uterine fibroids, include leuprolide/leuprorelin. Peptides that may be employed in compositions of the invention for use in the treatment of diabetes type 2 are amylins and fragments, exendins and fragments, insulin-like growth factors and fragments, gastric inhibitory polypeptides and fragments, chromogranin A, pancreastatin, insulin C-peptides, glucagons and glucagon-like peptides or ghrelin peptides, preferably GLP-1 receptor agonists including semaglutide, liraglutide, albiglutide or dulaglutide. Peptides that may be employed in compositions of the invention for use in the treatment of obesity are peptides acting as melanocortin receptor modulator or as GLP-1 receptor agonists. Peptides that may be employed in compositions of the invention for use in the treatment of endometriosis or uterine fibroids are peptides acting as GnRH agonists including buserelin, gonadorelin, goserelin, histrelin, leuprorelin, nafarelin or triptorelin and GnRH antagonists, such as abarelix, cetrorelix, degarelix, ganirelix, elagolix, relugolix and teverelix. Peptides that may be employed in compositions of the invention for use in the treatment of polycystic disease or hypotension or intractable diarrhoea or neuroendocrine tumors or carcinoid syndrome are peptides acting as SRIF agonists, such as octreotide, pasireotide or lanreotide.

In particular, peptides that may be employed in compositions of the invention for use in the treatment of urinary disorders are peptides selectively binding to V-2 receptors, such as desmopressin. There is thus provided a composition of the invention comprising desmopressin for use in the treatment of a urinary disorder.

Compositions of the invention that comprise bisphosphonates, such as alendronate, clodronate, etidronate, ibandronate, neridronate, olpadronate, pamidronate, risedronate, tiludronate and zoledronate, may be useful in the treatment of osteoporosis, including post-menopausal osteoporosis, with a view to decreasing the risk of bone fracture.

Compositions of the invention that comprise anaesthetics and/or sedatives, such as those mentioned hereinbefore are useful in anaesthesia and/or sedation. There is thus provided a composition of the invention comprising an anaesthetic for use in anaesthetizing a subject, and/or in the treatment of pain; as well as a composition of the invention comprising a sedative, for use in sedating a subject, and/or in the treatment of pain or anxiety. In particular, there is provided a composition of the invention comprising ketamine for use for use in sedating a subject, and/or in the treatment of pain or anxiety.

Compositions of the invention that comprise antidepressants, such as those mentioned hereinbefore, and especially brexanolone (post-partum depression), esketamine and ketamine, are useful in the treatment of depressive disorders. There is thus provided a composition of the invention comprising an antidepressant for use in the treatment of depression or a depressive disorder.

Compositions of the invention that comprise antihistamines, such as those mentioned hereinbefore, are useful in the treatment inflammation and/or allergy. There is thus provided a composition of the invention comprising an antihistamine for use in the treatment of inflammation and/or allergy.

Compositions of the invention that comprise analgesics such as those mentioned hereinbefore are useful in the treatment of pain. In particular, compounds that may be employed in compositions of the invention for use in such treatment include non-steroidal antiinflammatory drugs, such as ketorolac.

Compositions of the invention that comprise adrenergic receptor modulators, such as those mentioned hereinbefore are useful in the treatment of a variety of disorders, depending on the compound(s) that is/are included in such a composition. In particular, compositions of the invention comprising epinephrine (adrenaline) are useful in the treatment of, for example, allergic reactions, including extreme allergic reaction, such as anaphylactic shock to, for example, insect stings/bites, foodstuffs, drugs and/or other substances. There is thus provided a composition of the invention comprising epinephrine for use in the treatment of an allergic reaction, such as the treatment of anaphylactic shock.

Compositions of the invention that comprise dopaminergic receptors, such as those mentioned hereinbefore are useful in the treatment of a variety of disorders, depending on the compound(s) that is/are included in such a composition. In particular, compositions of the invention comprising apomorphine are useful in the treatment of, for example, Parkinson's disease and, in particular, the treatment of so-called 'wearing-off' episodes (i.e. motor fluctuations, such as muscle stiffness, loss of muscle control, etc.) in patients in patients with advanced Parkinson's disease and/ or receiving levodopa therapy. There is thus provided a composition of the invention comprising apomorphine for use in the treatment of Parkinson's disease, such as in the treatment of muscle stiffness and/or loss of muscle control in Parkinson's patients.

Compositions of the invention that comprise serotonergic receptors, such as those mentioned above hereinbefore are useful in the treatment of a variety of disorders, depending on the compound(s) that is/are included in such a composition. In particular, compositions of the invention comprising any one of the triptans mentioned hereinbefore are useful in the treatment of migraine. There is thus provided a composition of the invention comprising a triptan (such as almotriptan, eletriptan or, alternatively, rizatriptan, zolmitriptan, sumatriptan, frovatriptan or naratriptan) for use in the treatment of migraine.

Compositions of the invention that comprise one or more of the cardiovascular drugs mentioned hereinbefore, including one or more of the:

anticoagulants (Factor Xa inhibitors or platelet inhibitors);
α- and β-blockers, ACE inhibitors, angiotensin II receptor antagonists, neprilysin inhibitors, calcium channel blockers; diuretics, vasodilators, endothelin receptor antagonists, digitalis preparations and other hypertension treatments; and
HMG-CoA reductase inhibitors, are useful in the prevention or treatment of various cardiovascular disorders including, respectively:

conditions characterised by blood clots (including strokes, transient ischemic attacks, cardiac arrests, deep vein thrombosis, pulmonary embolisms, etc.),
conditions characterised by high blood pressure (including hypertension, angina, congestive heart failure, etc.); and
coronary heart disease (including high levels cholesterol and other lipids, such as low density lipoproteins and triglycerides, atherosclerosis, etc.

According to further aspects of the invention, there are provided compositions of the invention comprising:

one or more of the antivirals mentioned hereinbefore for use in the treatment of viral (e.g. hepatitis C) infections;
one or more of the erectile dysfunction drugs mentioned hereinbefore for use in the treatment of male of female sexual disorders, such as erectile dysfunction.

Compositions of the invention may also include, or may also be administered along with, one or more alkyl saccharides. Alkyl saccharides that may be employed include alkyl glycosides, which may be defined as any sugar joined by a linkage to an alkyl group, such as a $C_{7-18}$ alkyl glycoside. Alkyl glycosides thus may include alkyl maltosides (such as dodecyl maltoside), alkyl glucosides, alkyl sucrosides, alkyl thiomaltosides, alkyl thioglucosides, alkyl thiosucroses and alkyl maltotriosides. However, we prefer that the alkyl saccharide is a sugar ester.

Sugar esters that may be used in the compositions of the invention include trisaccharide esters, such as raffinose esters, monosaccharide esters, such as glucose esters, galactose esters and fructose esters, and/or, preferably, disaccharide esters, such as maltose esters, lactose esters, trehalose esters and, in particular, one or more sucrose esters.

Sucrose esters that may be employed in compositions of the invention have a hydrophilic-lipophilic balance value of between 6 and 20. The term 'hydrophilic-lipophilic balance' (HLB) is a term of art that will be well understood by those skilled in the art (see, for example, 'The HLB System: A Time-Saving Guide to Emulsifier Selection', published by ICI Americas Inc, 1976 (revised 1980), in which document, Chapter 7 (pages 20-21) provides a method of how to determine HLB values). The longer the fatty acid chains in the sucrose esters and the higher the degree of esterification, the lower the HLB value. Preferred HLB values are between 10 and 20, more preferably between 12 and 20.

Sucrose esters thus include $C_{8-22}$ saturated or unsaturated fatty acid esters, preferably saturated fatty acid esters and preferably $C_{10-18}$ fatty acid esters and most preferably $C_{12}$ fatty acid esters. Particularly suitable fatty acids from which such sucrose esters may be formed include erucic acid, behenic acid, oleic acid, stearic acid, palmitic acid, myristic acid and lauric acid. A particularly preferred such fatty acid is lauric acid. Commercially-available sucrose esters include those sold under the trademark Surfhope® and Ryoto® (Mitsubishi-Kagaku Foods Corporation, Japan).

Sucrose esters may be diesters or monoesters of fatty acids, preferably monoesters, such as sucrose monolaurate. The skilled person will appreciate that the term 'monolaurate' refers to a mono-ester of lauric acid, and that the terms 'lauric acid ester' and 'laurate' have the same meaning and can therefore be used interchangeably. Commercially available sucrose monolaurate products are also sometimes referred to as 'sucrose laurate'. Commercially-available sucrose monolaurate (or sucrose laurate) products, such as Surfhope® D-1216 (Mitsubishi-Kagaku Foods Corporation, Japan), which may contain small amounts of diesters and/or higher sucrose esters, and minor amounts of other sucrose esters and free sucrose, are suitable for use in the invention. The skilled person will understand that any reference to a specific sucrose ester herein includes commercially available products comprising that sucrose ester as a principle component.

Preferred sucrose esters contain only one sucrose ester, which means that a single sucrose ester (e.g. a commercially-available sucrose ester product) contains a single sucrose ester as the/a principle component (commercially available products may contain impurities, for example a monoester product may contain small amounts of diesters and/or higher esters, such products may be considered to 'contain only one sucrose ester' in the context of the present invention). As used herein, the term 'principle component' will be understood to refer to the major component (e.g. greater than about 50%, such as about 70% weight/weight or volume/volume) in a mixture of sucrose esters, such as commonly commercially available surfactant products, which are typically sold with a certain range of ester compositions.

A particularly preferred sucrose ester is sucrose monolaurate.

Whether included within a composition of the invention, or in a final dosage form including one or more compositions of the invention, amounts of alkyl saccharide that may be employed may be in the range of about 0.1% to about 10%, such as about 0.5% to about 5%, preferably about 0.75% to about 3% (e.g. to about 2%, such as about 1%), by weight, based upon the total weight of the composition.

Further, optional, additional excipients may be employed within, or administered along with, compositions of the invention, including one or more (further) surfactants. Surfactants that may be mentioned include polyoxyethylene esters (e.g. Myrj™), including polyoxyl 8 stearate (Myrj™ S8), polyoxyl 32 stearate (Gelucire® 48/16), polyoxyl 40 stearate (Myrj™ S40), polyoxyl 100 stearate (Myrj™ S100), and polyoxyl 15 hydroxystearate (Kolliphor® HS 15), polyoxyethylene alkyl ethers (e.g. Brij™), including polyoxyl cetostearyl ether (e.g. Brij™ CS12, CS20 and CS25), polyoxyl lauryl ether (e.g. Brij™ L9 and L23), and polyoxyl stearyl ether (e.g. Brij™ S10 and S20), and polyoxylglycerides (e.g. Gelucire®), including lauroyl polyoxylglycerides (Gelucire® 44/14) and stearoyl polyoxylglycerides (Gelucire® 50/13), sorbitan esters (e.g. Span™), including sorbitan monopalmitate (Span™ 40) and sorbitan monostearate (Span™ 60), polysorbates (Tweens™), including polysorbate 40 (polyoxyethylene (20) sorbitan monopalmitate), polysorbate 60 (polyoxyethylene (20) sorbitan monostearate) and polysorbate 20 (polyoxyethylene (20) sorbitan monolaurate), and sodium lauryl sulfate; and monoacyl glycerols (monoglycerides), such as 2-oleoylglycerol, 2-arachidonoylglycerol, monolaurin, glycerol monomyristate, glycerol monopalmitate, glyceryl hydroxystearate and, preferably, glycerol monostearate, glycerol monooleate (e.g. Cithrol®) and glycerol monocaprylate (e.g. Capmul®).

Other optional additional ingredients (excipients) that may be included within, or administered along with, compositions of the invention, include isotonicity and/or osmotic agents (e.g. sodium chloride), sterols (or steroid alcohols), such as cholesterol and phytosterols (e.g. campesterol, sitosterol, and stigmasterol); antioxidants (e.g. sodium metabisulfite or, in addition, α-tocopherol, ascorbic acid, potassium ascorbate, sodium ascorbate, ascorbyl palmitate, butylated hydroxytoluene, butylated hydroxyanisole, dodecyl gallate, octyl gallate, propyl gallate, ethyl oleate, monothioglycerol, vitamin E polyethylene glycol succinate, or thymol); chelating (complexing) agents (e.g. edetic acid (EDTA), citric acid, tartaric acid, malic acid, maltol and galactose, including salt forms of any of these agents); preservatives (e.g. benzalkonium chloride or, in addition, benzyl alcohol, boric acid, parabens, propionic acid, phenol, cresol, or xylitol); viscosity modifying agents or gelling agents (such as cellulose derivatives, including hydroxypropylcellulose, methylcellulose, hydroxypropyl methylcellulose, carboxymethylcellulose, etc., starches and modified starches, colloidal silicon dioxide, aluminium metasilicate, polycarbophils (e.g. Noveon®), carbomers (e.g. Carbopol®) and polyvinylpyrrolidone); mucoadhesive polymers, such as carboxymethyl cellulose, modified cellulose gum and sodium carboxymethyl cellulose (NaCMC); starch derivatives, such as moderately cross-linked starch, modified starch and sodium starch glycolate; crosslinked polyvinyl pyrollidone, acrylic polymers, such as carbomer and its derivatives (Polycarbophyl, Carbopol®, etc.); polyethylene oxide (PEO); chitosan (poly-(D-glucosamine)); natural polymers, such as gelatin, sodium alginate, pectin; scleroglucan; xanthan gum; guar gum; poly co-(methylvinyl ether/maleic anhydride); and croscarmellose (e.g. croscarmellose sodium); pH buffering agents (e.g. citric acid, maleic acid, malic acid, or glycine, or corresponding salts thereof, such as sodium citrate); colouring agents; penetration enhancers (e.g. isopropyl myristate, isopropyl palmitate, pyrrolidone, or tricaprylin); other lipids (neutral and polar); aromatic carboxylic acids, such as benzoic acid optionally substituted with one or more groups selected from methyl, hydroxyl, amino, and/or nitro, for instance, toluic acid or salicylic acid; and, if appropriate, flavourings (e.g. lemon, peppermint powder or, preferably, menthol), sweeteners (e.g. neohesperidin, acesulfame K or, preferably, sucralose) and dyestuffs.

Total amounts of such 'additional' excipients (including surfactants that are not an alkyl saccharide that may be present in compositions of the invention) that may be included with a composition of the invention per se (irrespective of the dosage form it is included in) may also be up to about 15% (e.g. about 10%), such as up to about 5%, by weight, based on the total weight of the composition.

Total amounts of such 'additional' excipients that may be included within a final dosage form including one or more compositions of the invention, may be up to about 99.99%, such as up to about 99.9%, including up to about 99%, for example up to about 90%, for example if the one or more additional excipients is a filler or a carrier in a tablet, a film or the like.

The skilled person will appreciate that, if any additional optional ingredients are included within compositions of the invention, the nature of those ingredients, and/or the amounts of those ingredients that are included, should not have a detrimental effect on the Tg of the composition for the reasons described hereinbefore. In this respect, such optional ingredients may be incorporated in the spray-drying process (i.e. mixed together along with the active ingredient and the carrier materials in the appropriate volatile solvent and then spray-dried), or may be included separately to the spray-dried plurality of particles.

According to a further aspect of the invention, there is provided the compositions of the invention for use in medicine (human and veterinary), and thus in the treatment of patients in need of medical treatment of a condition that the relevant active ingredient is known to treat.

By 'treatment' of such conditions, we include the prophylaxis or the diagnosis of such conditions, in addition to therapeutic, symptomatic and palliative treatment.

Compositions of the invention may be administered by any suitable dosing means that is known to the skilled person. Compositions of the invention may be administered transmucosally, and in particular intranasally, by way of a suitable nasal applicator, or a dispenser, means, which means is capable of administering a suitable dose of active ingredient in the form of one or more compositions of the invention to the nasal cavity.

A suitable nasal dosing means and/or applicator should thus be capable of housing, and storing, the one or more doses of the composition of the invention itself, or capable of being attached to a reservoir/container that houses and stores the one or more doses of the composition of the invention, and to do so without the consequence of a significant loss of physical and chemical integrity of the composition, including by way of ingress of water. In this way, the composition will be usable as soon as the applicator device is actuated by an end user (whether this is single dose or multiple dose usage), whereupon the applicator will deliver composition (e.g. powder) with an appropriate dose of active ingredient as defined herein to the nasal mucosa of a subject.

Appropriate applicator means have been described in the prior art. When used with compositions of the invention, such compositions may be loaded into a reservoir that is attached to, or forms part of, such an applicator means, where it is contained until the applicator means, or dispenser, is actuated. Hereinafter the terms 'applicator', 'dispenser', 'device' 'applicator means', 'dispensing means', 'applicator device', 'dispensing device' and 'insufflator' may be used interchangeably and mean the same thing.

Such applicator means may thus also include a mechanism for expelling the powder formulation from the reservoir through an exit means, which exit means includes anything sized for placement within a human nostril, such as an appropriately-shaped nozzle.

Thus, the applicator should be capable of providing a reproducible and sufficient amount of powder formulation in a single administration step (and in a manner in which the device does not require 'priming'), that will provide a therapeutic dose of active ingredient.

Nasal applicators/inhalation devices that may be employed to administer compositions of the invention in the form of powders may include multiple-dose applications, such as metered dose inhalation devices (MDIs), dry powder inhalation devices (DPIs; including low, medium and high resistant DPIs) and soft mist inhalation devices (SMIs) that may be adapted based on technology that is known in the field of delivery of active ingredients to the lung.

In MDIs, compositions of the invention should be capable of forming a stable suspension when suspended in solvents that are typically employed therein, such as a propellant, which propellant has a sufficient vapour pressure to form aerosols upon activation of the delivery device (e.g. a hydrocarbon, a fluorocarbon, a hydrogen-containing fluorocarbon, or a mixture thereof).

However, if the nasal applicator is a single dose applicator from which a composition is dispensed following actuation, and is then disposed of after use, suitable applicator means or devices for delivering single doses of active ingredients include those described in U.S. Pat. Nos. 6,398,074, 6,938,798 or 9,724,713, the relevant disclosures in all of which documents are incorporated herein by reference. FIGS. 1 and 2 of the present application are based on FIG. 1 and FIG. 2, respectively, of U.S. Pat. No. 6,398,074, and FIGS. 3 to 7 are based on FIG. 19 to FIG. 23, respectively, of U.S. Pat. No. 9,724,713. Both are illustrations of applicators that be may be employed to administer a composition of the invention intranasally.

In FIG. 1, the device comprises an upper body/dispenser head 1 incorporating an outlet channel 40 (i.e. part of the 'exit means' as hereinbefore described) and a gripping means 60 allowing the user to actuate the device. Inside the upper body/dispenser head 1 an element is mounted, designated in its assembly by reference number 2, that incorporates a reservoir 10 and an air chamber 22 for the air blast 20. It is possible for this element 2 to be produced in one piece with the body 1. A lower body 3 is also provided in order to be able to slide relative to the upper body 1 and relative to the element 2, the user exerting a push force on the lower body to actuate the device.

The reservoir 10 contains a single dose of a composition of the present invention. The reservoir 10 has an air inlet 11 and a product outlet 15. A product retention device 12, comprising a grid that is permeable to air, is disposed in the air inlet 11 to keep the product in the reservoir 10 until the composition is dispensed. The product outlet 15 is blocked, preferably in a sealed fashion, by a closing ball 16, which is removed from its blocking position by the flow of air when the applicator is actuated and the product is being dispensed.

When a user actuates the device, a pressure is exerted on the plunger 25 in such a way that the piston 21 compresses the air 20 contained in the chamber 22. Since the grid 12 is permeable to air, the compression of the air in chamber 22 creates a blast of air that is transmitted to the reservoir 10 and consequently is applied to the closing ball 16 which is blocking the product outlet 15.

The dimensions of the closing ball 16 and its fixing at the reservoir product outlet 15 are such that the ball 16 is removed from its blocking position, when a minimum predetermined pressure is created through the reservoir 10 by way of a blast of the air 20.

The pre-compression created by the closing ball 16 ensures that when it is removed from its blocking position, the energy accumulated in the hand of the user is such that the piston 21 integral with the plunger 25 is propelled within the chamber 22 thereby creating a powerful blast of air 20, that is to say an air flow suitable to finely spray the dose of composition of the invention.

When this minimum pressure is reached, the ball is quickly moved towards the outlet channel 40 of the device and the flow of air 20 created by the blast expels substantially all of the dose of composition of the invention that is contained within the reservoir 10.

Preferably, the outlet channel 40 has a diameter greater than the diameter of the closing ball 16 in order to allow the dose of product to be expelled through the outlet channel 40 by flowing around the ball 16. As shown in FIG. 2, which represents the same device after actuation, the channel 40 comprises a means 41 of arresting or fixing the ball 16 in order to prevent its expulsion out of the device when the product is being expelled.

A further embodiment that may be employed to administer compositions of the invention intranasally is provided in U.S. Pat. No. 9,724,713 at column 7, line 50 to column 8, line 61 and FIGS. 19 to 23, which are reproduced as FIGS. 3 to 7 of the present application.

In this embodiment, the reservoir 10 is secured in the upper body/dispenser head 1 which includes the dispenser outlet channel 40 (i.e. part of the 'exit means' as hereinbefore described), which has gripping means or finger rest 60, which allows the user to actuate the device. A radial shoulder 37 (see FIG. 5) of the upper body/dispenser head 1 advantageously defines the assembled position of the reservoir 10 in said of the upper body/dispenser head 1.

The mechanical opening system includes a set of rods 61, 62, wherein a second rod portion 62 is pushed by said first rod portion 61 when the device is actuated. At the end of their actuation stroke, i.e. in the dispensing position, the set of rods 61, 62 co-operate with the closure element 16, which is spherical, in particular a ball as in the first embodiment discussed above, so as to expel it mechanically from its closed position.

In this embodiment, the piston 21 is separate from the first rod portion 61, and slides both relative to the air chamber 22 and to a cylindrical surface 614 that is secured to the first rod portion 61. FIG. 7 is a diagrammatic perspective view of the air expeller of the device in FIGS. 3 to 6, in its rest position.

The air chamber 22 may thus be cylindrical, and in its rest position is put into communication with the surrounding air at fluting or grooves 615 that are formed in said cylindrical surface 614 and that co-operate with the piston 21, in particular in its rest position. The piston 21 thus includes an inner lip 215 that slides in airtight manner over the cylindrical wall 614 during actuation, and that co-operates with said fluting 615 in its rest position. The piston 21 also includes an axial extension 216 that co-operates with a top edge 251 of the pusher element 25 (termed a 'plunger' in the first embodiment) that moves said piston 21 in the air chamber 22 during actuation.

A retainer member 42 is extended downwards by an axial extension 43 that comes into contact with the top axial end 610 of the first rod portion 61 during actuation.

In addition, in this embodiment, there is no outer body, but merely a cover 27 that is assembled on the bottom axial edge of the air chamber 22.

A spring 80 is provided between the radial flange 225 of the air chamber 22 and the part that forms the first rod portion 61 and the cylindrical surface 614, so as to return the air expeller automatically into its rest position after actuation.

The operating principle is as follows. In the rest position in FIG. 3, the reservoir 10 is closed in sealed manner by the retainer member 42 and by the closure element/ball 16. The air expeller is open to the atmosphere by co-operation between the inner lip 215 of the piston 21 and the fluting 615 of the cylindrical surface 614.

When it is desired to actuate the device, the user presses on the pusher element 25. During this initial stroke, the inner lip 215 of the piston leaves the fluting 615 so as to come to co-operate in airtight manner with the cylindrical surface 614, thereby closing the air chamber 22. At the same moment, the top edge 251 of the pusher element comes into contact with the axial extension 216 of the piston 21, and the top axial end 610 of the first rod portion 61 comes into contact with the axial extension 43 of the retainer member 42.

Figure 4:
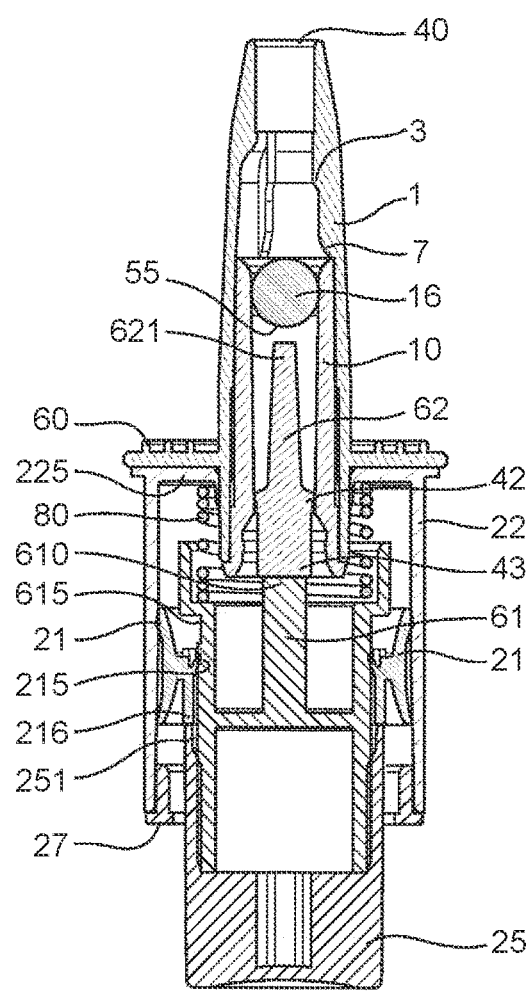

However, the top axial end 621 of the second rod portion 62 is still not in contact with the rounded surface 55 of the closure element/ball 16, as can be seen in FIG. 4.

Continued actuation thus simultaneously moves the piston 21 in the air chamber, thereby compressing the air contained therein, and moves the retainer member 42 away from its position of closing the reservoir 10. When the second rod portion 62 contacts the rounded surface 55 of the closure element/ball 16, said closure element/ball is expelled mechanically from its closed position, so as to enable the composition to be expelled under the effect of the air compressed by the air expeller.

The dispensing position is shown in FIG. 5. As can be seen in FIG. 5, the retainer member 42 may become detached from the first rod portion 61 while the composition is being expelled under the effect of the compressed air provided by the air expeller. In this position, said closure element/ball is expelled out from the reservoir 10 so as to enable the fluid or powder to be dispensed under the effect of the compressed air. The closure element/ball 16 thus becomes jammed in splines 3 of the upper body/dispenser head 1, which splines prevent in particular any risk of said closure element/ball 16 being expelled out from said upper body dispenser head 1.

When the user relaxes the device, as shown in FIG. 6, the spring 80 that was compressed during actuation, returns the first rod portion 61 towards its rest position. This creates suction that sucks the closure element 16 and the retainer member 42 back towards, or close to, their closure positions. This thus blocks the path for new suction so as to avoid soiling the air expeller while it returns automatically into its rest position, with the empty reservoir still assembled on the air expeller. However, the piston 21 remains in its dispensing position as a result of friction with the air chamber 22 and of the suction created in the reservoir 30, such that the cylindrical surface 614 slides over the inner lip 215 of the piston until said inner lip co-operates once again with the fluting 615. At this moment, the air chamber 22 is once again in communication with the surrounding air, and suction is no longer created by the return into the rest position. The piston 21 is thus also entrained towards its rest position. This makes it possible to close the reservoir after use.

Optionally, the unit formed by the upper body/dispenser head 1 and the empty reservoir 10 could be removed from the air expeller and replaced by a new unit that includes a full reservoir.

Appropriate applicator devices that may be used include those available from Aptar Pharma, France (UDS Monopowder). Other examples of applicator devices that may be used in conjunction with compositions of the invention (especially those in the form of powders) include those described in US patent application US 2011/0045088A, U.S. Pat. No. 7,722,566 (see e.g. FIGS. 1 and 7) and U.S. Pat. No. 5,702,362 and international patent application WO 2014/004400, the relevant disclosures of which documents are hereby incorporated by reference.

According to a further aspect of the invention, there is provided a process for the manufacturing of an applicator device comprising a composition of the invention, wherein said process comprises the step of loading said composition into a reservoir within or adjunct to said applicator device.

According to another aspect of the invention, there is provided an applicator and/or dispenser device comprising one or more compositions of the invention in the form of a powder, which applicator or device may be actuated one or more times to deliver one or more compositions of the invention, each comprising an appropriate dose of active ingredient, upon each such actuation, which applicator/dispenser device comprises: an outlet through which at least one composition is dispensed;

a means of externally generating a force (e.g. an air-flow) upon actuation of the device by a user;

at least one (optionally replaceable) reservoir that contains said one or more compositions of the invention, which reservoir is, or is capable of being placed, in direct or indirect communication with the dispenser outlet;

a displaceable, optionally reversible, sealing means in the device and/or the reservoir for retaining the one or more compositions within the reservoir until a composition is dispensed;

a mechanical opening system that co-operates with said sealing means such that a single composition of the invention is expelled mechanically by the forcing means when the device is actuated; and optionally, a mechanism for re-sealing the device and/or the reservoir to retain further compositions within the reservoir until a further composition is to be dispensed.

According to a still further aspect of the invention there is provided an applicator and/or dispenser device comprising a single dose of a composition of the invention, suitable for dispensing that composition, which applicator/dispenser device comprises:

a dispenser outlet;

an air expeller for generating a flow of air while the device is being actuated, said air expeller including a piston that slides in an air chamber between a rest position and a dispensing position;

said piston slides in airtight manner within said air chamber;

at least one reservoir that contains a dose of a composition of the invention, said reservoir including an air inlet that is connected to said air expeller;

a composition outlet that is connected to said dispenser outlet;

said air inlet including a displaceable sealing means (e.g. a retainer member) for retaining the composition in the reservoir until the composition is dispensed;

said composition outlet being closed by a closure element that is fitted in the composition outlet of the reservoir;

said device further including a mechanical opening system that co-operates with said closure element so as to expel it mechanically from its closed position while the device is being actuated; and said piston of said air expeller, when in its rest position, co-operating in non-airtight manner with said air chamber.

In the latter aspect of the invention, it is preferred that:
(i) the air chamber within which said piston slides in airtight manner is substantially cylindrical;
(ii) the closure element is force fitted in the composition outlet of the reservoir;
(iii) said air chamber is in communication with the atmosphere in the rest position; and/or
(iv) said piston includes an inner lip that is suitable for co-operating with a cylindrical surface, said cylindrical surface includes fluting that co-operates in non-airtight manner with said inner lip of the piston in its rest position.

Such a nasal applicator or dispensing device is capable of providing for an appropriate and reproducible powder spray pattern and/or plume geometry that enables efficient delivery of said powder to the nasal cavity (e.g. a nostril).

In compositions of the invention, mean particle sizes may be presented as weight-, number-, or volume-, based mean diameters. As used herein, the term 'weight based mean diameter' will be understood by the skilled person to include that the average particle size is characterised and defined from a particle size distribution by weight, i.e. a distribution where the existing fraction (relative amount) in each size class is defined as the weight fraction, as obtained by e.g. sieving (e.g. wet sieving). The term 'volume based mean diameter' is similar in its meaning to weight based mean diameter, but will be understood by the skilled person to include that the average particle size is characterised and defined from a particle size distribution by volume, i.e. a distribution where the existing fraction (relative amount) in each size class is defined as the volume fraction, as measured by e.g. laser diffraction. As used herein, the term 'number based mean diameter' will be understood by the skilled person to include that the average particle size is characterised and defined from a particle size distribution by number, i.e. a distribution where the existing fraction (relative amount) in each size class is defined as the number fraction, as measured by e.g. microscopy. Other instruments that are well known in the field may be employed to measure particle size, such as equipment sold by e.g. Malvern Instruments, Ltd (Worcestershire, UK), Sympatec GmbH (Clausthal-Zellerfeld, Germany) and Shimadzu (Kyoto, Japan).

Although particle size is not (or rather may not be) critical when compositions of the invention are formulated for administration e.g. perorally, topically, to the oral, ocular or other mucosae, or by injection or infusion, powder compositions of the invention will typically have a volume-based mean diameter (VMD) within the range of about 0.2 μm, such as about 0.5 μm (e.g. about 1 μm) up to about 1,000 μm (e.g. up to about 500 μm, such as about 400 nm or about 500 nm), and the appropriate particle size range may be selected based on the dosage form in which it is intended to include such compositions.

However, the skilled person will understand that, to allow for effective intranasal administration, powders will typically have a volume-based mean diameter (VMD) within the range of about 5 μm up to about 300 μm (e.g. up to about 200 μm). Depending on the applicator device that is employed, the VMD may be in the range of about 10 μm to about 100 μm, such as about 20 μm to about 60 μm.

Preferred particle size distributions for intranasal drug delivery may also include those in which the D10 is above about 3 μm and below about 75 μm (e.g. up to about 50 μm), such as greater than about 10 μm, and the D90 is between about 80 μm and about 1,000 μm (e.g. about 500 μm), such as less than about 100 μm. The skilled person will understand that the parameter 'D10' (or Dv(10)') means the size (or diameter) in a particle size distribution below which 10% of the total volume of material in the sample is contained. Similarly, the 'D90' (or Dv(90)') means the size below which 90% of the material is contained.

By powders having particle size distributions and VMDs within the above ranges, we include the bulk VMD and/or the emitted VMD, that is the particle size distribution when initially loaded into the device and/or when it is expelled therefrom, respectively.

Particle sizes may be measured by standard equipment, such as a dry (or a wet) particle size measurement technique, including dry dispersion technologies available from manufacturers such as Sympatec and Malvern.

Preferred particle shapes include spherical or substantially spherical, by which we mean that the particles possess an aspect ratio smaller than about 20, more preferably less than about 10, such as less than about 4, and especially less than about 2, and/or may possess a variation in radii (measured from the centre of gravity to the particle surface) in at least about 90% of the particles that is no more than about 50% of the average value, such as no more than about 30% of that value, for example no more than about 20% of that value.

Nevertheless, particles may be any shape, including irregular shaped (e.g. 'raisin'-shaped), needle-shaped, disc-shaped or cuboid-shaped, particles. For a non-spherical particle, the size may be indicated as the size of a corresponding spherical particle of e.g. the same weight, volume or surface area.

The spray angle of emitted (dispensed) powder composition of the invention from a nasal applicator and/or a dispenser device should preferably be less than about 90°.

Wherever the word 'about' is employed herein in the context of amounts, for example absolute amounts, such as doses, weights, volumes, sizes, diameters, aspect rations, angles, etc., or relative amounts (e.g. percentages) of individual constituents in a composition or a component of a composition (including concentrations and ratios), timeframes, and parameters such as temperatures, pressure, relative humidities, etc., it will be appreciated that such variables are approximate and as such may vary by ±10%, for example ±5% and preferably ±2% (e.g. ±1%) from the actual numbers specified herein. This is the case even if such numbers are presented as percentages in the first place (for example 'about 10%' may mean±10% about the number 10, which is anything between 9% and 11%).

Compositions of the invention have the advantage that they are capable of being stored over a wide range of temperatures. Thus, compositions of the invention may be subject to low temperatures (e.g. below freezing) without impacting the amount of active ingredient that is administered to a subject. Further, compositions of the invention may have the advantage that they are more physically and chemically stable at higher temperature than relevant prior art compositions.

Compositions of the invention further may also have the advantage that they provide for higher bioavailability of active ingredients compared to prior art compositions. The compositions of the invention may provide for this higher bioavailability alongside a more rapid absorption, which will likely lead to a more rapid onset of action than such prior art and/or commercially-available compositions, and thus meets a significant medical need.

The compositions, pharmaceutical formulations, uses and methods described herein may also have the advantage that, in the treatment of the conditions for which the relevant active ingredient is known for, they may be more convenient for the first responder, physician and/or patient than, be more efficacious than, be less toxic than, have a broader range of activity than, be more potent than, produce fewer side effects than, have a lower inter-patient variability, or that it/they may have other useful pharmacological properties over, similar formulations or methods (treatments) known in the prior art, whether for use in the treatment of those conditions by transmucosal, such as intranasal, administration or otherwise.

The invention is illustrated but in no way limited by way of the following examples with reference to the figures.

Example 1

Spray-Dried Epinephrine (Adrenaline) Formulation

Adrenaline bitartrate (0.729 g; Fisher Scientific, Sweden), along with α-D-lactose monohydrate (0.500 g; DFE Pharma, Germany), maltodextrin (Glucidex IT 12 DE; 1.247 g; Roquette, France), and sucrose monolaurate D-1216 (0.025 g; Mitsubishi-Kagaku Foods Corporation, Japan), were dispensed (in total 2.50 g) into a glass flask and dissolved in MQ-water (47.50 g) by stirring at room temperature.

The resultant mixture was fed into a spray-dryer (Pro-CepT, Belgium) equipped with an ultrasonic nozzle operating at 25 kHz. The feed rate of the spray-dryer was set at 3.0 g/minute, the inlet temperature was set at 180° C., the gas flow was set at 300 L/min, and the cyclone gas was set at 1.5 bar.

The resultant spray-dried powder was collected as a fine, dry, and free-flowing, with a nominal dose of 4 mg adrenaline free base in 25 mg powder.

The powder was analyzed for particle size distribution (PSD) by dry powder laser diffraction. The sample was dispersed with an Aero S dry dispersing unit (with compressed air at 0.5 bar) before sizing with a Mastersizer 3000 laser diffraction sensor (both Malvern Panalytical, UK), as shown in Table 1 below.

TABLE 1

| | |
|---|---|
| Dv(10) (μm) | 12.9 |
| Dv(50) (μm) | 23.9 |
| Dv(90) (μm) | 42.0 |

The PSD of the adrenaline formulation was well within a distribution suitable for nasal administration.

The assay and purity of the spray-dried adrenaline formulation was determined by HPLC/UV analysis. The assay was 99.7%, and the percentage of the total related substances (% RS) (i.e. impurities and degradation products) was less than 0.29%.

Example 2

Spray-Dried Apomorphine Formulation

Spray-drying of an aqueous solution (50.00 g) comprising apomorphine hydrochloride (0.114 g; Johnson Matthey, UK), α-D-lactose monohydrate (0.500 g), maltodextrin (Glucidex IT 12 DE; 1.861 g), and sucrose monolaurate D-1216 (0.025 g) using the general procedure described in Example 1 above resulted in a fine, dry, and free-flowing, powder, with a nominal dose of 1 mg apomorphine free base in 25 mg powder.

Analysis of the powder for PSD as described in Example 1 above by dry powder laser diffraction is shown in Table 2 below and was determined to be well within a distribution suitable for nasal administration.

TABLE 2

| | |
|---|---|
| Dv(10) (μm) | 16.3 |
| Dv(50) (μm) | 29.1 |
| Dv(90) (μm) | 50.0 |

The assay and purity, as determined by HPLC/UV analysis, was 103.7% with a % RS of less than 0.38%.

Example 3

Spray-Dried Loxapine Formulation

The general procedure described in Example 1 above was employed to spray-dry an aqueous solution (62.50 g) comprising loxapine succinate (0.205 g; Tiefenbacher, Germany), along with α-D-lactose monohydrate (0.500 g), maltodextrin (Glucidex IT 12 DE; 1.771 g), and sucrose monolaurate D-1216 (0.025 g) to produce a fine, dry and free-flowing powder with a nominal dose of 1.5 mg loxapine free base in 25 mg powder.

The PSD of the resultant powder was determined as described in Example 1 and is shown in Table 3 below. It was well within a distribution suitable for nasal administration.

TABLE 3

| | |
|---|---|
| Dv(10) (μm) | 13.9 |
| Dv(50) (μm) | 26.7 |
| Dv(90) (μm) | 48.4 |

The assay and purity, as determined by HPLC/UV analysis, was 100.2% with a % RS of less than 0.05%.

Example 4

Spray-Dried Ketorolac Formulation

The general procedure described in Example 1 above was employed to spray-dry an aqueous solution (50.02 g) comprising ketorolac tromethamine (0.737 g; Uquifa, ES), along with α-D-lactose monohydrate (0.500 g), maltodextrin (Glucidex IT 12 DE; 1.771 g), and sucrose monolaurate D-1216 (0.025 g), to produce a fine, dry and free-flowing powder with a nominal dose of 5 mg ketorolac free acid in 25 mg powder.

The PSD of the resultant powder was determined as described in Example 1 and is shown in Table 4 below and, again, was well within a distribution suitable for nasal administration.

TABLE 4

| | |
|---|---|
| Dv(10) (μm) | 12.6 |
| Dv(50) (μm) | 22.7 |
| Dv(90) (μm) | 39.2 |

The assay and purity, as determined by HPLC/UV analysis, was 103.0% with a % RS of less than 0.22%.

Example 5

Chemical Stability of Spray-Dried Powders

Amounts of between 105 and 115 mg of the spray-dried powders from Examples 1 to 4 above were dispensed into 1.5 mL glass vials closed with screw-caps. For each powder, two vials were placed inside a climate cabinet at 40° C. and 75% relative humidity (40/75). One vial was placed in the cabinet as it was, and one vial was further packaged in a heat-sealed aluminium sachet.

The chemical stability of three of the drug substances (adrenaline, apomorphine and loxapine) after 6 month, and for ketorolac after 2 months, with total amounts of impurities and degradation products expressed as % RS, is summarized for the different compositions and packaging in Table 5 below.

TABLE 5

| | Vial only (% RS) | | | |
|---|---|---|---|---|
| Formulation | Initial | 1 month | 3 months | 6 months |
| Example 1 | 0.29 | 2.27 | 8.22 | 25.27 |
| Example 2 | 0.38 | 0.17 | 0.21 | 0.28 |
| Example 3 | 0.05 | 0.10 | 0.27 | 0.74 |
| | | 2 weeks | 1 month | 2 months |
| Example 4 | 0.22 | 0.40 | 0.54 | 1.33 |
| | Aluminium Sachet (% RS) | | | |
| Formulation | Initial | 1 month | 3 months | 6 months |
| Example 1 | 0.29 | 1.55 | 4.23 | 12.49 |
| Example 2 | 0.38 | 0.16 | 0.20 | 0.25 |
| Example 3 | 0.05 | 0.09 | 0.18 | 0.78 |
| | | 2 weeks | 1 month | 2 months |
| Example 4 | 0.22 | 0.34 | 0.42 | 1.89 |

The observed changes in % RS for these sensitive active ingredients, primarily in relation to Example 3 and, particularly, to Example 2, show that chemical stability of drug substances is surprisingly good when formulated in compositions of the invention.

Example 6

Pharmacokinetic Study in Dogs After Nasal and Intramuscular Administration of Adrenaline The purpose of the study was to obtain and evaluate basic pharmacokinetic profiles after nasal administration of the composition of Example 1, and after intramuscular administration of adrenaline in an aqueous solution.

The study was conducted in six Beagle dogs, three males and three females, of about 15-18 months age. The dogs were dosed in a cross-over dosing regimen to compensate for potential sequence effects. Dosing was always performed in the morning and the dogs had been fasted overnight (minimum 8 hours). Water was supplied ad libitum, and feed was given 4 hours after administration.

Each dog was given the composition of Example 1 nasally at a dose of 4 mg/animal (IN 4 mg), and adrenaline in an aqueous solution (1 mg/mL) at a dose of 0.3 mg/animal (IM 0.3 mg). The composition of Example 1 was administered intranasally by the specific intranasal device from Aptar Pharma, France (UDS Monopowder).

The aqueous solution of adrenaline was administered intramuscularly into the left back leg musculature (musculus quadriceps femoris). The wash-out period between each administration was 48 hours.

The in vivo part of the investigation was made in compliance with the European Convention for the Protection of Vertebrate Animals used for Experimental and other Scientific Purposes (ETS No. 123).

Blood samples were collected under conventional aseptic conditions by venepuncture from v. cephalica antebrachic or v. saphena from all dogs at specified time points. A volume of 1 mL was collected in plastic Vacuette® tubes containing $K_3EDTA$. The blood samples were kept on ice before centrifuged at 3500 rpm for 10 min at +4° C.

Plasma was extracted and transferred to pre-labelled cryovials containing Na metasulfite as an antioxidant and stored at −80° C. before transportation for bioanalysis. Scheduled sampling time points were: −5 (pre-dose), 2.5, 5, 10, 15, 20, 30, 45, 60 and 90 minutes after administration.

The frozen plasma samples were transported to Recipharm OT, Uppsala, Sweden, for bioanalysis. Plasma concentrations of adrenaline were determined by using HPLC-MS-MS analysis capable of measuring concentrations of adrenaline in dog plasma within the range of 0.05 to 100 ng/mL using adrenaline-D6 as the deuterated internal standard. The analytes were extracted from the sample plasma using protein precipitation with TCA. After centrifugation the supernatant was used for analysis.

All samples were analysed by first separating analytes using Acquity HSS T3 column (2.1 mm*100 mm, 1.7 μm) and subsequently detecting them using positive electrospray ionization and multiple reaction monitoring (MRM). Quantification was performed in the range 0.05 to 100 ng/mL.

Figure 8:
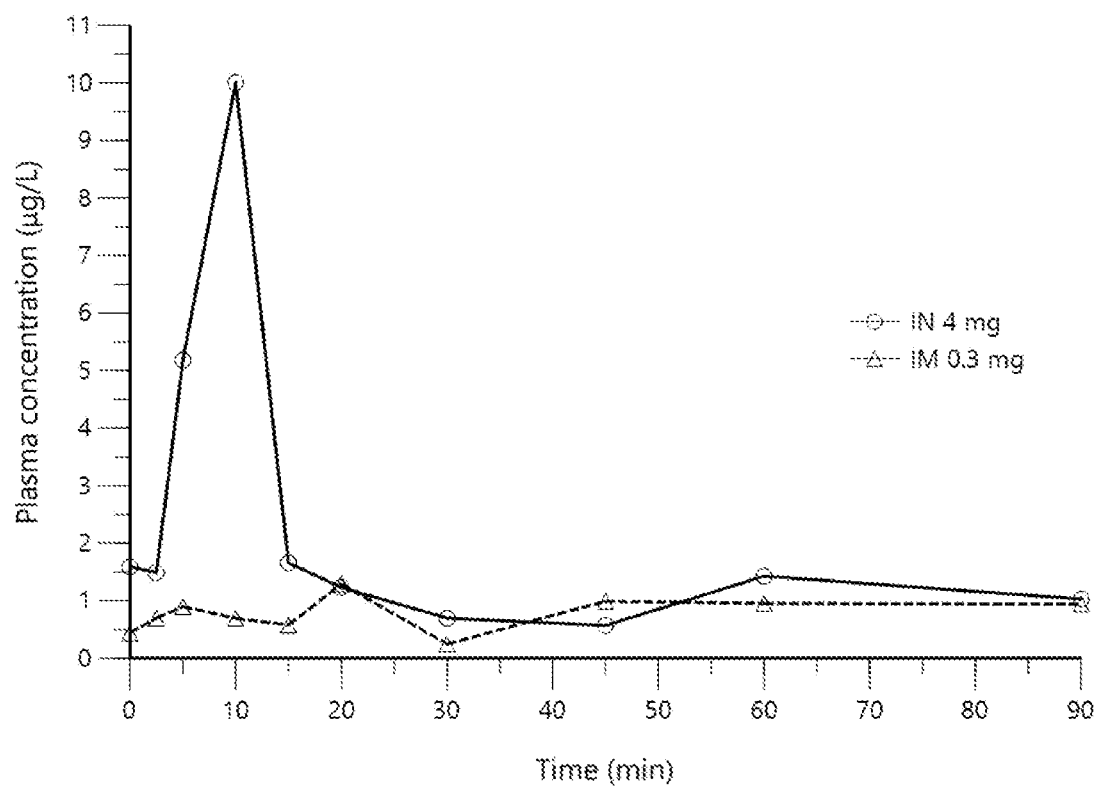
FIGS. 8 to 11 show plasma concentration-time curves from a pharmacokinetic study carried out in dogs, in which intranasally-administered compositions of the invention comprising different active ingredients are compared with plasma concentration-time curves for the same active ingredients delivered via different administration means.

Pharmacokinetic parameters were calculated by non-compartmental analysis using Phoenix VVinNonlin (v8.0), and are presented in Table 6 below and FIG. 8, in which $AUC_{last}$ is the area under the curve of plasma concentration versus time, up to the last sampling point; $C_{max}$ is the highest measureable concentration after administration and $t_{max}$ is the time to highest measureable concentration. All values presented in Table 6-9 are mean values of N=6.

TABLE 6

| | $AUC_{last}$ (min*μg/L) | $C_{max}$ (μg/L) | $t_{max}$ (min) |
|---|---|---|---|
| Example 1 4 mg nasal administration | 143.28 | 10.76 | 10.83 |
| Aqueous sol. 0.3 mg i.m. administration | 72.15 | 1.83 | 34.58 |

Example 7

Pharmacokinetic Study in Dogs After Nasal and Intramuscular Administration of Apomorphine Essentially the same procedure as that described in Example 6 above was carried out, with each dog being given the composition of Example 2 intranasally at a dose of 1 mg/animal (IN 1 mg), and an injected aqueous solution of apomorphine (5 mg/mL) at a dose of 1 mg/animal (IM 1 mg).

The scheduled sampling time points were: 0 (pre-dose), 2.5, 5, 10, 20, 30, 45, 60, 90, 120 and 240 minutes after administration.

Plasma concentrations of apomorphine were determined by measuring concentrations of apomorphine in dog plasma using apomorphine-D5 as the deuterated internal standard. Quantification was performed in the range 0.10 to 300 ng/mL.

Figure 9:
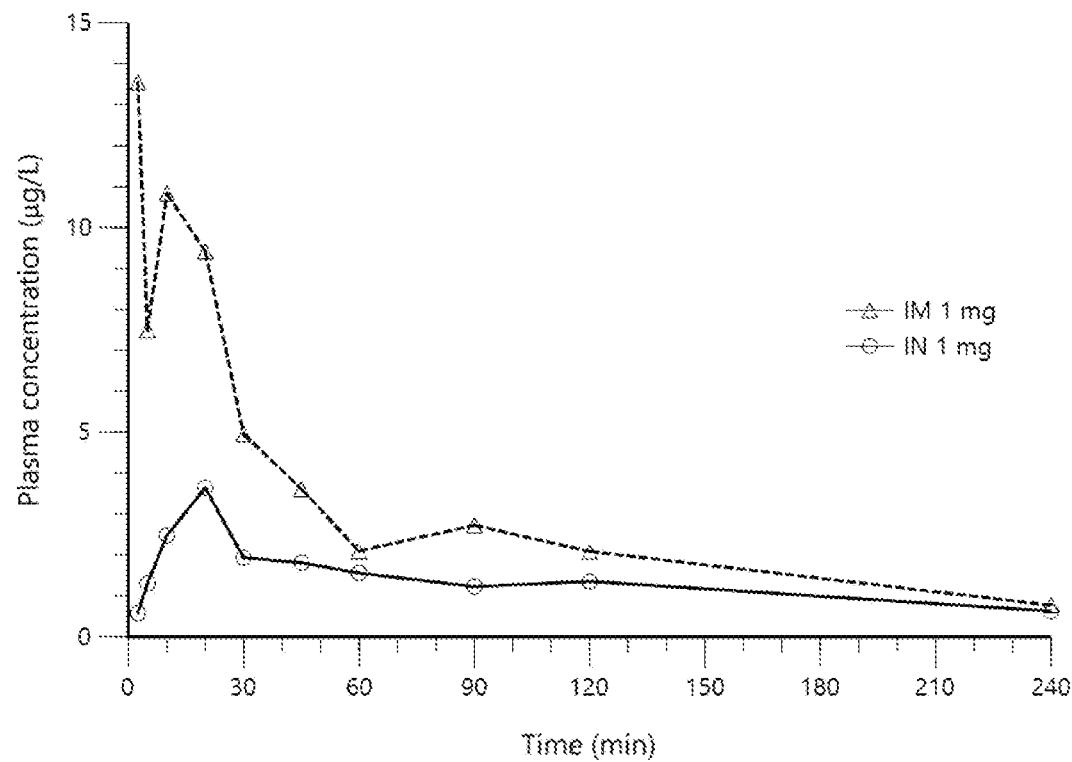

Pharmacokinetic parameters are presented in Table 7 below and FIG. 9.

TABLE 7

|  | $AUC_{last}$ (min*µg/L) | $C_{max}$ (µg/L) | $t_{max}$ (min) |
| --- | --- | --- | --- |
| Example 2 1 mg nasal administration | 313.41 | 4.29 | 40.00 |
| Aqueous sol. 1 mg i.m. administration | 657.10 | 19.26 | 13.75 |

Example 8

Pharmacokinetic Study in Dogs After Nasal and Intramuscular Administration of Loxapine Essentially the same procedure as that described in Example 6 above was carried out, with each dog being given the composition of Example 3 intranasally at a dose of 1.5 mg/animal (IN 1.5 mg), and an injected aqueous solution of loxapine (3 mg/mL) at a dose of 1.5 mg/animal (IM 1.5 mg).

Plasma was extracted and transferred to pre-labelled Eppendorf tubes and stored at −20° C., or below, before transportation for bioanalysis. Scheduled sampling time points were: 0 (pre-dose), 2.5, 5, 10, 20, 30, 45, 60, 120, 240 and 480 minutes after administration.

Plasma concentrations of loxapine were determined using loxapine-D8 as the deuterated internal standard. Quantification was performed in the range 0.3 to 300 ng/mL.

Figure 10:
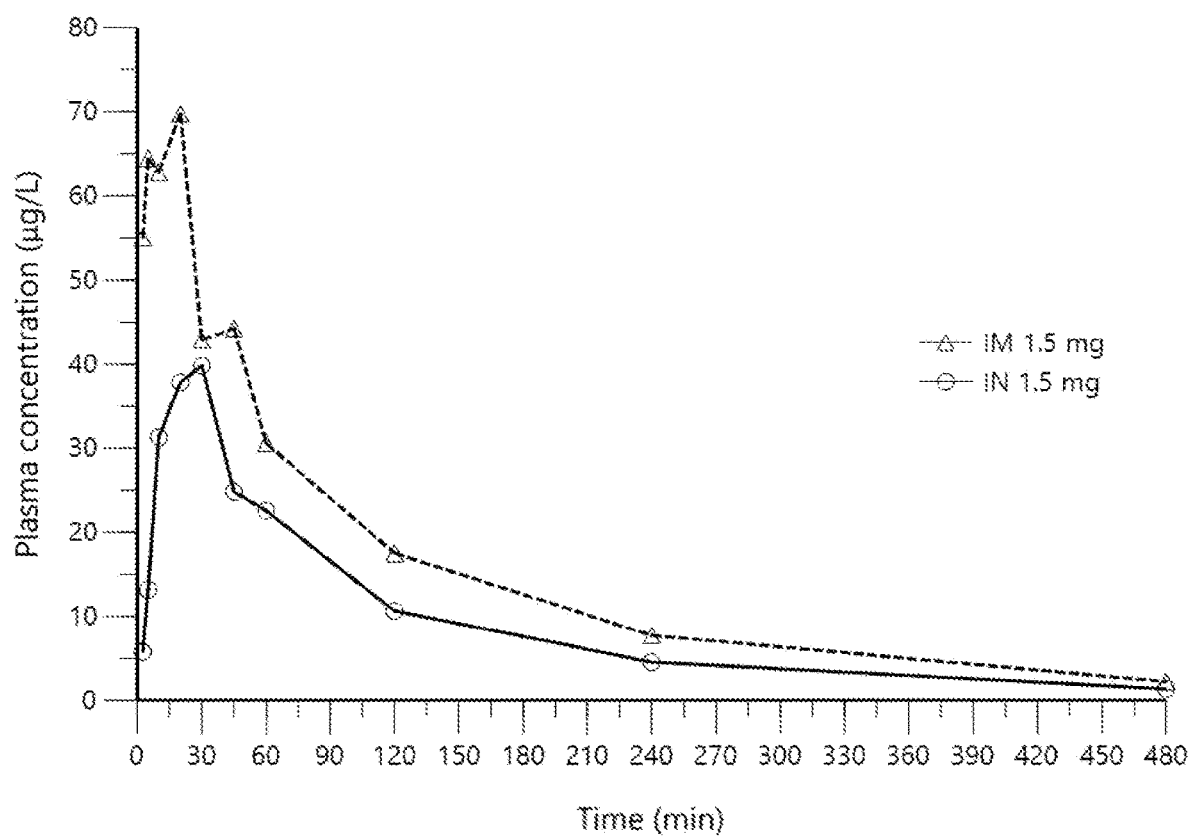

Pharmacokinetic parameters are presented in Table 8 below and FIG. 10.

TABLE 8

|  | $AUC_{last}$ (min*µg/L) | $C_{max}$ (µg/L) | $t_{max}$ (min) |
| --- | --- | --- | --- |
| Example 3 1.5 mg nasal administration | 4107 | 43.88 | 23.33 |
| Aqueous sol. 1.5 mg i.m. administration | 6781 | 84.07 | 14.58 |

Example 9

Pharmacokinetic Study in Dogs After Nasal and Oral Administration of Ketorolac

Essentially the same procedure as that described in Example 6 above was carried out, with each dog being given the composition of Example 4 intranasally at a dose of 5 mg/animal (IN 5 mg), and a ketorolac oral tablet at a dose of 5 mg/animal (PO 5 mg). Ketorolac tablets were administered perorally with approximately 3 mL of water via a syringe to ensure that the tablet was correctly swallowed and complete esophageal clearance.

Plasma was extracted and transferred to pre-labelled Eppendorf tubes and stored at −20° C. or below, before transportation for bioanalysis. Scheduled sampling time points were: 0 (pre-dose), 2.5, 5, 10, 20, 30, 45, 60, 90, 150 and 300 minutes after administration.

Plasma concentrations of R-ketorolac and S-ketorolac were determined by using enantioselective HPLC-MS-MS analysis capable of measuring concentrations of R- and S-ketorolac in dog plasma within using ketorolac-D3 as the deuterated internal standard.

All samples were analysed by first separating analytes using LUX Amylose-1 chiral column (2.0 mm*50 mm, 3.0 µm) and subsequently detecting them using positive electrospray ionization and multiple reaction monitoring (MRM). Quantification was performed in the range 0.50 to 5000 ng/mL.

Figure 11:
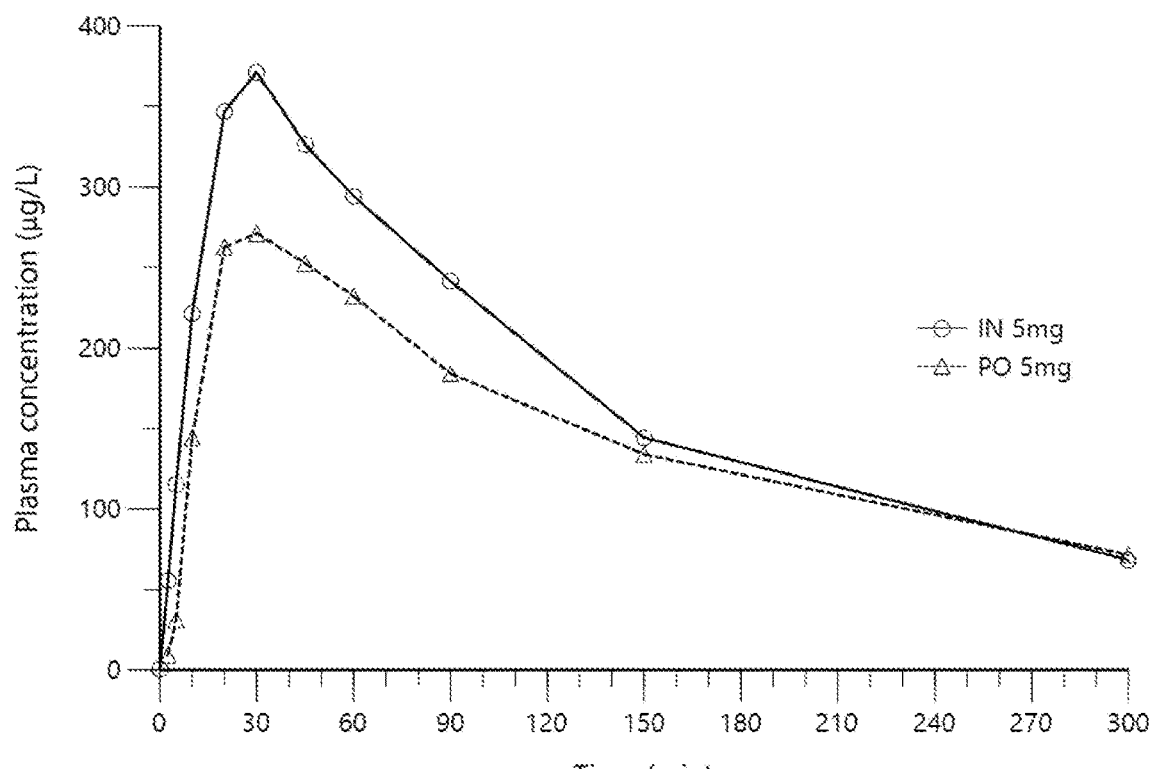
Figure 11:
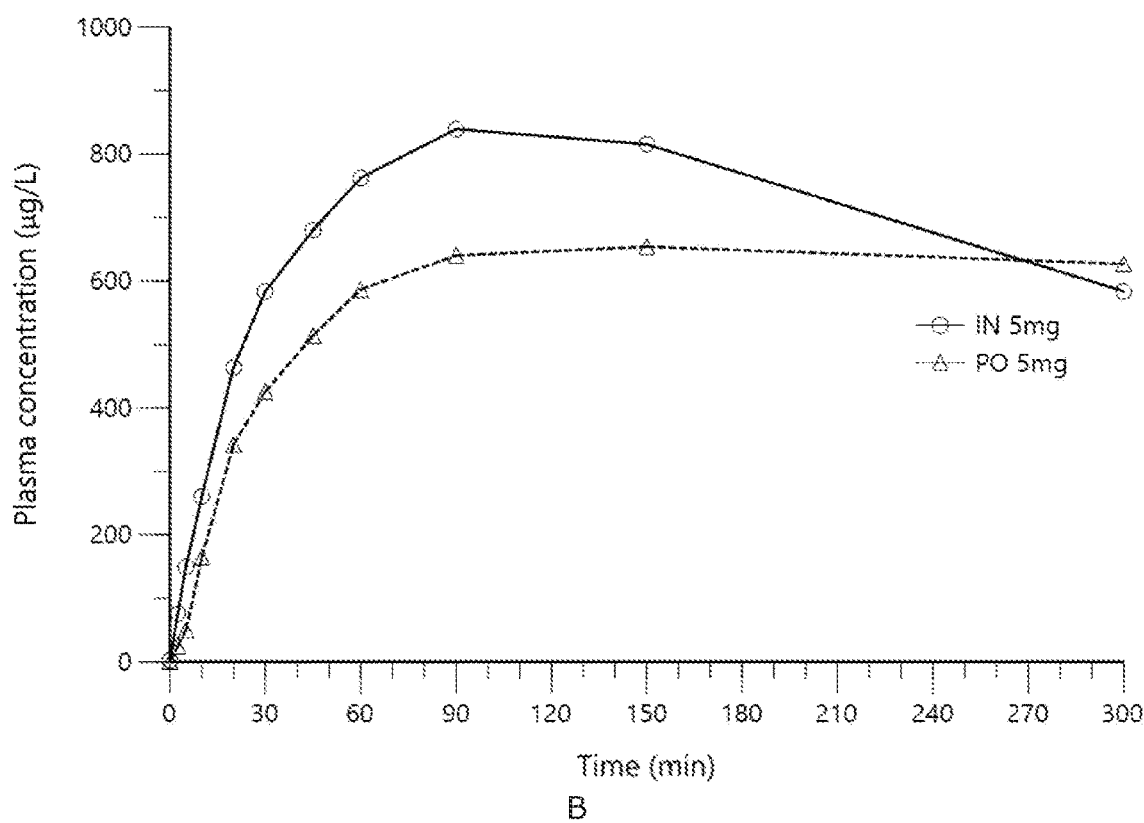

Pharmacokinetic parameters are presented in Table 9 below and FIG. 11 (A; R-enantiomer and B; S-enantiomer).

TABLE 9

|  | R-ketorolac | | | S-ketorolac | | |
| --- | --- | --- | --- | --- | --- | --- |
|  | $AUC_{last}$ (min * µg/L) | $C_{max}$ (µg/L) | $t_{max}$ (min) | $AUC_{last}$ (min * µg/L) | $C_{max}$ (µg/L) | $t_{max}$ (min) |
| Example 4 5 mg nasal administration | 51680 | 418 | 43.33 | 206900 | 903 | 135 |
| Tablet 5 mg oral administration | 43200 | 319 | 40.83 | 175400 | 739 | 145 |

Example 10

Chemical Stability of Spray-Dried Apomorphine Formulation

An equivalent procedure to that described in Example 2 above was carried out to produce a powder with an assay and purity, as determined by HPLC/UV analysis, was 105.6% with a % RS of less than 0.01%.

A chemical stability experiment essentially as described in Example 5 above was carried out by packaging vials containing the apomorphine formulation in heat-sealed aluminium sachets together with a desiccant.

The chemical stability of apomorphine after 1 and 3 months storage, with total amounts of impurities and degradation products expressed as % RS, is summarized for the different compositions and packaging in Table 10 below.

TABLE 10

| (% RS) | | |
| --- | --- | --- |
| Initial | 1 month | 3 months |
| 0.01 | 0.05 | 0.06 |

The observed changes in % RS for the sensitive active ingredient apomorphine, show that chemical stability of drug substance is surprisingly good when formulated in compositions of the invention.

Example 11

Chemical Stability of Different Spray-Dried Loxapine Formulations

The general procedure as described in Example 1 above was employed to spray-dry different aqueous solutions (62.50 g) comprising loxapine succinate (0.204 g), along with α-D-lactose monohydrate (0.500 g), as well as maltodextrin (Glucidex IT 12 DE; 1.771 g) and sucrose monolaurate D-1216 (0.025 g) (Example A);

maltodextrin (Glucidex IT 12 DE; 1.696 g), and sucrose monolaurate D-1216 (0.100 g) (Example B); and HPMC (Methocel K3; 1.771 g; IMCD Nordic, Sweden), and sucrose monolaurate D-1216 (0.025 g), in each case producing a fine, dry and free-flowing powder with a nominal dose of 1.5 mg loxapine free base in 25 mg powder.

The initial assay and purity, as determined by HPLC/UV analysis, was:

102.0% with a % RS of less than 0.06% for Example A;

101.4% with a % RS of less than 0.06% for Example B; and 101.9% with a % RS of less than 0.09% for Example C.

A chemical stability experiment essentially as described in Example 5 above was carried out by packaging vials containing the different loxapine formulation in heat-sealed aluminium sachets with a dessicant.

The chemical stability after 1, 3, and 6 months, with total amounts of impurities and degradation products expressed as % RS, is summarized for the different compositions in Table 11 below.

TABLE 11

| Formulation | Aluminium Sachet (% RS) | | | |
| --- | --- | --- | --- | --- |
| | Initial | 1 month | 3 months | 6 months |
| Example A | 0.06 | 0.14 | 0.11 | 0.17 |
| Example B | 0.06 | 0.16 | 0.13 | 0.16 |
| Example C | 0.09 | 0.15 | 0.10 | 0.18 |

The observed changes in % RS for this sensitive active ingredient show that chemical stability of drug substance is surprisingly good when formulated in compositions of the invention.

Example 12

Different Epinephrine (Adrenaline) Formulations Produced by Spray-Drying in Air

Eight aqueous solutions (each 50 g; Examples D to L, respectively) comprising dry matter compositions each with 0.364 g of adrenaline bitartrate, and with respective amounts of the excipients lactose monohydrate, maltodextrin (Glucidex IT 12 DE), HPMC (Methocel K3), sucrose monolaurate (D-1216), sodium metabisulfite, (Merck Chemical & Lifescience AB, Sweden) and/or disodium EDTA (Titriplex® III; Merck Chemical & Lifescience AB, Sweden), as shown in grams in Table 12 below, were spray dried by the general procedure described in Example 1 above, to produce fine, dry and free-flowing powders with a nominal dose of 1.0 mg adrenaline free base in 25 mg powder.

TABLE 12

| Example | Lactose | Maltodextrin | HPMC | Sucrose mono-laurate | Na Meta-bisulfite | EDTA |
|---|---|---|---|---|---|---|
| D | 1.000 | 3.486 | 0 | 0.150 | 0 | 0 |
| E | 1.000 | 2.615 | 0.872 | 0.150 | 0 | 0 |
| F | 1.000 | 3.446 | 0 | 0.150 | 0.040 | 0 |
| G | 2.000 | 2.486 | 0 | 0.150 | 0 | 0 |
| H | 2.000 | 1.865 | 0.622 | 0.150 | 0 | 0 |
| I | 1.000 | 3.137 | 0.349 | 0.150 | 0 | 0 |
| J | 1.000 | 3.101 | 0.345 | 0.150 | 0.040 | 0 |
| K | 2.000 | 2.237 | 0.249 | 0.150 | 0 | 0 |
| L | 1.000 | 3.466 | 0 | 0.150 | 0 | 0.020 |

The PSD of the resultant powders was determined as described in Example 1 and is shown in Table 13 below and, again, was well within a distribution suitable for nasal administration (NA means 'not analysed').

TABLE 13

| Example | Dv(10) (μm) | Dv(50) (μm) | Dv(90) (μm) |
|---|---|---|---|
| D | 16.8 | 35.8 | 66.8 |
| E | 23.7 | 43.0 | 73.7 |
| F | 16.1 | 36.6 | 69.0 |
| G | 16.6 | 33.2 | 61.4 |
| H | NA | | |
| I | 20.5 | 42.2 | 73.9 |
| J | 18.9 | 38.2 | 68.9 |
| K | NA | | |
| L | 15.9 | 34.6 | 65.4 |

The initial assay and purity (expressed as % RS), as determined by HPLC/UV analysis, is presented in Table 14 below.

TABLE 14

| Example | Assay (%) | % RS |
|---|---|---|
| D | 105.1 | 0.25 |
| E | 105.9 | 0.16 |
| F | 101.7 | 0.05 |
| G | 104.5 | 0.25 |
| H | 100.6 | 0.09 |
| I | 101.1 | 0.11 |
| J | 101.6 | 0.10 |
| K | 101.9 | 0.08 |
| L | 101.5 | 0.06 |

A chemical stability experiment was carried out essentially as described in Example 5 above by packaging vials containing different adrenaline formulation in heat-sealed aluminium sachets together with a desiccant, and storing them in climate cabinets at 40/75.

The chemical stability after 1 month, with total amounts of impurities and degradation products expressed as % RS, is summarized for the different compositions in Table 15 below.

TABLE 15

| Formulation | Aluminium Sachet (% RS) | |
| --- | --- | --- |
| | Initial | 1 month |
| D | 0.25 | 0.06 |
| E | 0.16 | 0.08 |
| G | 0.25 | 0.09 |
| I | 0.11 | 0.06 |
| L | 0.06 | 0.05 |

The observed changes in % RS for the easily degraded adrenaline show that chemical stability of drug substances is surprisingly good when formulated in compositions of the invention.

Example 13

Different Epinephrine (Adrenaline) Formulations Produced by Spray-Drying Under Nitrogen Five aqueous solutions (each 50 g; Examples M to Q respectively) comprising dry matter compositions each with 0.218 g of adrenaline bitartrate, and with respective amounts of the excipients lactose monohydrate, maltodextrin (Glucidex IT 12 DE), HPMC (Methocel K3), sucrose monolaurate (D-1216) and/or sodium metabisulfite, as shown in grams in Table 16 below, were spray dried by the general procedure described in Example 1 above, except that nitrogen was employed as the drying gas instead of air, to produce fine, dry and free-flowing powders with a nominal dose of 1.0 mg adrenaline free base in 25 mg powder.

TABLE 16

| Example | Lactose | Maltodextrin | HPMC | Sucrose monolaurate | Na metabisulfite |
| --- | --- | --- | --- | --- | --- |
| M | 0.600 | 2.092 | 0 | 0.090 | 0 |
| N | 0.600 | 1.569 | 0.523 | 0.090 | 0 |
| O | 0.600 | 2.068 | 0 | 0.090 | 0.024 |
| P | 1.200 | 1.492 | 0 | 0.090 | 0 |
| Q | 1.200 | 1.119 | 0.373 | 0.090 | 0 |

The initial assay and purity (expressed as % RS), as determined by HPLC/UV analysis, is presented in Table 17 below.

TABLE 17

| Example | Assay (%) | % RS |
| --- | --- | --- |
| M | 103.1 | 0.05 |
| N | 102.8 | 0.06 |
| O | 103.6 | 0.14 |
| P | 101.0 | 0.09 |
| Q | 101.2 | 0.10 |

Example 14

Different Eletriptan Formulations Produced by Spray-Drying Under Nitrogen

Five ethanol/water solutions (each 80 g; Examples R to V respectively)) are made by dissolving the relevant excipients (as listed below) in 20 g of water, and separately dissolving eletriptan hydrobromide in 60 g of ethanol 70% v/v, and then adding the water solution comprising dissolved excipients to the ethanol solution comprising the active ingredient. The dry matter compositions each with 0.727 g of eletriptan hydrobromide (Tiefenbacher, Germany), and with respective amounts of the excipients lactose monohydrate, maltodextrin (Glucidex IT 12 DE), HPMC (Methocel K3), sucrose monolaurate (D-1216) and/or sodium metabisulfite, as shown in grams in Table 18 below, are spray dried by the general procedure described in Example 1 above, except that nitrogen is employed as the drying gas instead of air, to produce fine, dry and free-flowing powders with a nominal dose of 5.0 mg eletriptan free base in 25 mg powder.

TABLE 18

| Example | Lactose | Maltodextrin | HPMC | Sucrose monolaurate | Na metabisulfite |
| --- | --- | --- | --- | --- | --- |
| R | 0.600 | 1.583 | 0 | 0.090 | 0 |
| S | 0.600 | 1.187 | 0.396 | 0.090 | 0 |
| T | 0.600 | 1.559 | 0 | 0.090 | 0.024 |
| U | 1.200 | 0.983 | 0 | 0.090 | 0 |
| V | 1.200 | 0.737 | 0.246 | 0.090 | 0 |

The assay and purity are determined by HPLC/UV analysis and the PSD of the resultant powder is determined as described in Example 1 and is within a distribution suitable for nasal administration.

Example 15

Spray-Dried Formulations Comprising Opioid Antagonists

Five aqueous solutions (each 50 g; Examples W to AA respectively) as set out in Table 19 below (with respective amounts of the active ingredient (naltrexone hydrochloride (0.443 g; Mallinckrodt, UK) or nalmefene hydrochloride (1.91 g; Mallinckrodt, UK)), and the excipients lactose monohydrate, maltodextrin (Glucidex IT 12 DE), HPMC (Methocel K3) and/or sucrose monolaurate (D-1216) shown in grams, were spray dried by the general procedure described in Example 1 above, to produce fine, dry and free-flowing powders with nominal doses of 4 mg naltrexone in 25 mg powder, and 1.5 mg nalmefene in 22.5 mg powder.

TABLE 19

| Example | API | Lactose | Maltodextrin | HPMC | Sucrose monolaurate |
| --- | --- | --- | --- | --- | --- |
| W | Naltrexone | 0.500 | 1.531 | — | 0.025 |
| X | Naltrexone | 0.500 | — | 1.531 | 0.025 |
| Y | Nalmefene | 5.09 | 8.85 | — | 0.24 |
| Z | Nalmefene | 5.09 | — | 17.49 | 0.24 |
| AA | Nalmefene | 14.1 | — | 8.74 | 0.24 |

The initial assay and purity (expressed as % RS), as determined by HPLC/UV analysis, is presented in Table 20 below.

TABLE 20

| Example | Assay (%) | % RS |
|---|---|---|
| W | 99.7 | 0.25 |
| X | 104.1 | 0.16 |
| Y | 100.8 | 0.06 |
| Z | 99.3 | 0.13 |
| AA | 99.4 | 0.06 |

A chemical stability experiment essentially as described in Example 5 above was carried out by packaging vials containing the different formulation in heat-sealed aluminium sachets with a dessicant.

The chemical stability after 1, 3, and 6 months, with total amounts of impurities and degradation products expressed as % RS, is summarized for the different compositions in Table 21 below.

TABLE 21

| | Aluminium Sachet (% RS) | | | |
|---|---|---|---|---|
| Example | Initial | 1 month | 3 months | 6 months |
| W | 0.25 | 0.23 | 0.31 | 0.41 |
| X | 0.16 | 0.27 | 0.63 | 0.84 |
| Y | 0.06 | NA | 0.16 | NA |
| Z | 0.13 | NA | 0.24 | NA |
| AA | 0.06 | NA | 0.16 | NA |

The observed changes in % RS for these active ingredients show that chemical stability of drug substance is surprisingly good when formulated in accordance with the invention.

Example 16

Spray-Dried Desmopressin Formulation

The general procedure described in Example 1 above is employed to spray-dry an aqueous solution (125 g) comprising desmopressin acetate trihydrate (0.0025 g; Bachem, Switzerland), along with α-D-lactose monohydrate (5.000 g), maltodextrin (Glucidex IT 12 DE; 7.123 g), and sucrose monolaurate D-1216 (0.375 g) to produce a fine, dry and free-flowing powder with a nominal dose of 5 µg desmopressin in 25 mg powder.

The assay and purity are determined by HPLC/UV analysis and the PSD of the resultant powder is determined as described in Example 1 and is well within a distribution suitable for nasal administration.

Example 17

Spray-Dried Olanzapine Formulation

An ethanol/water solution (80 g) is made by dissolving the excipients α-D-lactose monohydrate (1.000 g), maltodextrin (Glucidex IT 12 DE; 1.100 g), HPMC (Methocel K3; 0.125 g), and sucrose monolaurate D-1216 (0.075 g) in 20 g water, and separately dissolving olanzapine (0.200 g; Tiefenbacher, Germany) in 60 g ethanol 70% v/v, and then adding the water solution comprising dissolved excipients to the ethanol 70% v/v solution comprising dissolved olanzapine. The general procedure described in Example 1 above is employed to spray-dry the ethanol/water solution (80 g) to produce a fine, dry and free-flowing powder with a nominal dose of 2 mg olanzapine free base in 25 mg powder.

The assay and purity are determined by HPLC/UV analysis and the PSD of the resultant powder is determined as described in Example 1 and is well within a distribution suitable for nasal administration.

The invention claimed is:

1. A nasal applicator device for intranasal delivery of a composition to nasal mucosa, wherein the device comprises a reservoir that is within, or adjunct or attached to, said device, which reservoir contains a composition in the form of an amorphous powder, which amorphous powder comprises particles, is free of liquid propellant, and is essentially free of water,
wherein said amorphous powder comprises:
(a) a pharmacologically-effective dosage amount of epinephrine or a pharmaceutically-acceptable salt thereof as sole active ingredient; and
(b) a pharmaceutically-acceptable carrier material, which carrier material comprises a combination of a disaccharide and a polymeric material comprising a dextrin and/or hydroxypropylmethyl cellulose;
wherein the particles of the amorphous powder comprise an amorphous composite of epinephrine or salt thereof and the carrier material; and
wherein the nasal applicator device is configured and the particles are of a size whereby said device, upon actuation, is capable of depositing an effective dose of epinephrine, or salt thereof, to the nasal mucosa.

2. The nasal applicator device as claimed in claim 1, wherein the amorphous powder comprises less than about 5% of water.

3. The nasal applicator device as claimed in claim 1, wherein the amorphous powder comprises less than about 3% or water.

4. The nasal applicator device as claimed in claim 1, wherein the amorphous powder comprises less than about 2% of water.

5. The nasal applicator device as claimed in claim 1, wherein the amorphous powder comprises less than about 1% of water.

6. The nasal applicator device as claimed in claim 1, wherein the disaccharide is selected from the group consisting of maltitol, trehalose, sucralose, sucrose, isomalt, maltose and lactose.

7. The nasal applicator device as claimed in claim 6, wherein the disaccharide comprises lactose or trehalose.

8. The nasal applicator device as claimed in claim 1, wherein the dextrin comprises a cyclodextrin or a maltodextrin.

9. The nasal applicator device as claimed in claim 1, wherein the carrier material comprises a combination of:
(i) lactose or trehalose; and
(ii) a maltodextrin.

10. The nasal applicator device as claimed in claim 1, wherein the ratio of disaccharide:polymeric material by weight is in the range of about 2:1 and about 1:8.

11. The nasal applicator device as claimed in claim 10, wherein the ratio of disaccharide:polymeric material by weight is about 2:1.

12. The nasal applicator device as claimed in claim 1, wherein the lowest measurable glass transition temperature of the composition is at least about 40° C. when measured at a relative humidity of up to about 35%.

13. The nasal applicator device as claimed in claim 1, wherein the composition further comprises a sucrose ester.

14. The nasal applicator device as claimed in claim 13, wherein the sucrose ester comprises sucrose monolaurate.

15. The nasal applicator device as claimed in claim 1, wherein the pharmacologically-effective dosage amount of epinephrine is between about 0.1 mg and about 5 mg (calculated as the free base compound).

16. The nasal applicator device as claimed in claim 1, wherein the nasal applicator device is a single-use device and the reservoir contains a single dose of said amorphous powder.

17. The nasal applicator device as claimed in claim 1, wherein the powder has a particle size distribution that includes a D10 that is above about 3 μm.

18. The nasal applicator device as claimed in claim 17, wherein the particle size distribution includes a D10 above about 10 μm.

19. The nasal applicator device as claimed in claim 18, wherein the particle size distribution includes a D90 below about 500 μm.

20. The nasal applicator device as claimed in claim 18, wherein the particle size distribution includes a D90 below about 100 μm.

21. The nasal applicator device as claimed in claim 1, wherein the powder has a particle size distribution that includes a volume-based mean diameter within the range of about 10 μm and about 100 μm.

22. The nasal applicator device as claimed in claim 1, wherein the carrier material comprises a combination of:
    (i) lactose or trehalose, and
    (ii) a maltodextrin; and
    wherein the amorphous powder composition further comprises sucrose monolaurate.

23. The nasal applicator device as claimed in claim 1, wherein the carrier material comprises a combination of:
    (i) lactose or trehalose, and
    (ii) a maltodextrin; and
    wherein the amorphous powder composition further comprises sucrose monolaurate, and the powder has a particle size distribution that includes a D10 above about 10 μm.

24. The nasal applicator device as claimed in claim 1, which is packaged within a container that substantially prevents the ingress of atmospheric water.

25. The nasal applicator device as claimed in claim 24, wherein the container comprises a material selected from the group of heat-sealed aluminium pouches and thermoformed plastics.

26. The nasal applicator device as claimed in claim 22, which is packaged within a container that substantially prevents the ingress of atmospheric water.

27. The nasal applicator device as claimed in claim 26, wherein the container comprises a material selected from the group of heat-sealed aluminium pouches and thermoformed plastics.

28. The nasal applicator device as claimed in claim 23, which is packaged within a container that substantially prevents the ingress of atmospheric water.

29. The nasal applicator device as claimed in claim 28, wherein the container comprises a material selected from the group of heat-sealed aluminium pouches and thermoformed plastics.

30. The nasal applicator device as claimed in claim 2, wherein the disaccharide is selected from the group consisting of maltitol, trehalose, sucralose, sucrose, isomalt, maltose and lactose.

31. The nasal applicator device as claimed in claim 30, wherein the disaccharide comprises lactose or trehalose.

32. The nasal applicator device as claimed in claim 2, wherein the dextrin comprises a cyclodextrin or a maltodextrin.

33. The nasal applicator device as claimed in claim 2, wherein the carrier material comprises a combination of:
    (i) lactose or trehalose; and
    (ii) a maltodextrin.

34. The nasal applicator device as claimed in claim 2, wherein the ratio of disaccharide:polymeric material by weight is in the range of about 2:1 and about 1:8.

35. The nasal applicator device as claimed in claim 34, wherein the ratio of disaccharide:polymeric material by weight is about 2:1.

36. The nasal applicator device as claimed in claim 2, wherein the lowest measurable glass transition temperature of the composition is at least about 40° C. when measured at a relative humidity of up to about 35%.

37. The nasal applicator device as claimed in claim 2, wherein the composition further comprises a sucrose ester.

38. The nasal applicator device as claimed in claim 37, wherein the sucrose ester comprises sucrose monolaurate.

39. The nasal applicator device as claimed in claim 2, wherein the pharmacologically-effective dosage amount of epinephrine is between about 0.1 mg and about 5 mg (calculated as the free base compound).

40. The nasal applicator device as claimed in claim 2, wherein the nasal applicator device is a single-use device and the reservoir contains a single dose of said amorphous powder.

41. The nasal applicator device as claimed in claim 2, wherein the powder has a particle size distribution that includes a D10 that is above about 3 μm.

42. The nasal applicator device as claimed in claim 41, wherein the particle size distribution includes a D10 above about 10 μm.

43. The nasal applicator device as claimed in claim 42, wherein the particle size distribution includes a D90 below about 500 μm.

44. The nasal applicator device as claimed in claim 42, wherein the particle size distribution includes a D90 below about 100 μm.

45. The nasal applicator device as claimed in claim 2, wherein the powder has a particle size distribution that includes a volume-based mean diameter within the range of about 10 μm and about 100 μm.

46. The nasal applicator device as claimed in claim 2, wherein the carrier material comprises a combination of:
    (i) lactose or trehalose, and
    (ii) a maltodextrin; and
    wherein the amorphous powder composition further comprises sucrose monolaurate.

47. The nasal applicator device as claimed in claim 2, wherein the carrier material comprises a combination of:
    (i) lactose or trehalose, and
    (ii) a maltodextrin; and
    wherein the amorphous powder composition further comprises sucrose monolaurate, and the powder has a particle size distribution that includes a D10 above about 10 μm.

48. The nasal applicator device as claimed in claim 2, which is packaged within a container that substantially prevents the ingress of atmospheric water.

49. The nasal applicator device as claimed in claim 48, wherein the container comprises a material selected from the group of heat-sealed aluminium pouches and thermoformed plastics.

50. The nasal applicator device as claimed in claim 46, which is packaged within a container that substantially prevents the ingress of atmospheric water.

51. The nasal applicator device as claimed in claim 50, wherein the container comprises a material selected from the group of heat-sealed aluminium pouches and thermoformed plastics.

52. The nasal applicator device as claimed in claim 47, which is packaged within a container that substantially prevents the ingress of atmospheric water.

53. The nasal applicator device as claimed in claim 52, wherein the container comprises a material selected from the group of heat-sealed aluminium pouches and thermoformed plastics.

54. A process for the manufacturing of the nasal applicator device as claimed in claim 1, which comprises loading said amorphous powder into the reservoir of said applicator device.

* * * * *